(12) United States Patent
Boubes

(10) Patent No.: US 11,938,307 B2
(45) Date of Patent: *Mar. 26, 2024

(54) LOCKING HEMODIALYSIS NEEDLE ASSEMBLY WITH INTEGRAL NEEDLE TIP PROTECTOR

(71) Applicant: Khaled Boubes, Dublin, OH (US)

(72) Inventor: Khaled Boubes, Dublin, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/108,175

(22) Filed: Feb. 10, 2023

(65) Prior Publication Data

US 2023/0191040 A1    Jun. 22, 2023

Related U.S. Application Data

(63) Continuation of application No. 16/792,385, filed on Feb. 17, 2020, now Pat. No. 11,590,293.

(Continued)

(51) Int. Cl.
*A61M 5/32* (2006.01)
*A61M 5/31* (2006.01)
*A61M 5/34* (2006.01)

(52) U.S. Cl.
CPC ........ *A61M 5/3202* (2013.01); *A61M 5/3286* (2013.01); *A61M 5/34* (2013.01);
(Continued)

(58) Field of Classification Search
CPC .... A61M 5/3202; A61M 5/3286; A61M 5/34; A61M 2005/3115; A61M 2005/3131;
(Continued)

(56) References Cited

U.S. PATENT DOCUMENTS 6,626,868 B1    9/2003  Prestidge et al.
2002/0147428 A1  10/2002 Chang et al.
(Continued)

OTHER PUBLICATIONS

Notification of Transmittal of the International Search Report and Written Opinion of the International Searching Authority, or the Declaration for International Application No. PCT/US2020/018478 dated Apr. 29, 2020, pp. 1-13.

*Primary Examiner* — Ariana Zimbouski
*Assistant Examiner* — Rachel T. Smith
(74) *Attorney, Agent, or Firm* — Nancy R Gamburd; Gamburd Law Group LLC

(57) ABSTRACT

A needle assembly for medical or surgical use is disclosed, such as for hemodialysis. A representative needle assembly comprises an outer needle assembly and an integral needle tip protector. A representative outer needle assembly comprises: an outer needle comprising: a first lumen; a first aperture with a sharp needle tip at a first distal end of the outer needle; and a second aperture arranged opposite the first aperture. In another embodiment, the outer needle has a longitudinal slot and the integral needle tip protector includes a sliding connector which is slidable in the longitudinal slot. The integral needle tip protector is arranged within the first lumen and moveable between a retracted configuration and an extended configuration, and comprises: a needle tip cover arranged to shield the sharp needle tip in the extended configuration, the needle tip cover having a smooth or beveled distal surface forming a blunt tip.

20 Claims, 17 Drawing Sheets

Related U.S. Application Data

(60) Provisional application No. 62/808,331, filed on Feb. 21, 2019.

(52) U.S. Cl.
CPC ............... *A61M 2005/3115* (2013.01); *A61M 2005/3131* (2013.01); *A61M 2005/3212* (2013.01)

(58) Field of Classification Search
CPC .. A61M 2005/3212; A61M 2005/3107; A61M 25/0612; A61M 2005/311; A61B 17/3494; A61B 17/3496; A61B 17/3417; A61B 2090/0801; A61B 2017/3454
See application file for complete search history.

(56) References Cited

U.S. PATENT DOCUMENTS

| | | | |
|---|---|---|---|
| 2002/0169420 A1* | 11/2002 | Galt | A61B 17/00491 606/171 |
| 2014/0018740 A1 | 1/2014 | Carlyon et al. | |
| 2016/0022312 A1 | 1/2016 | Tang et al. | |

\* cited by examiner

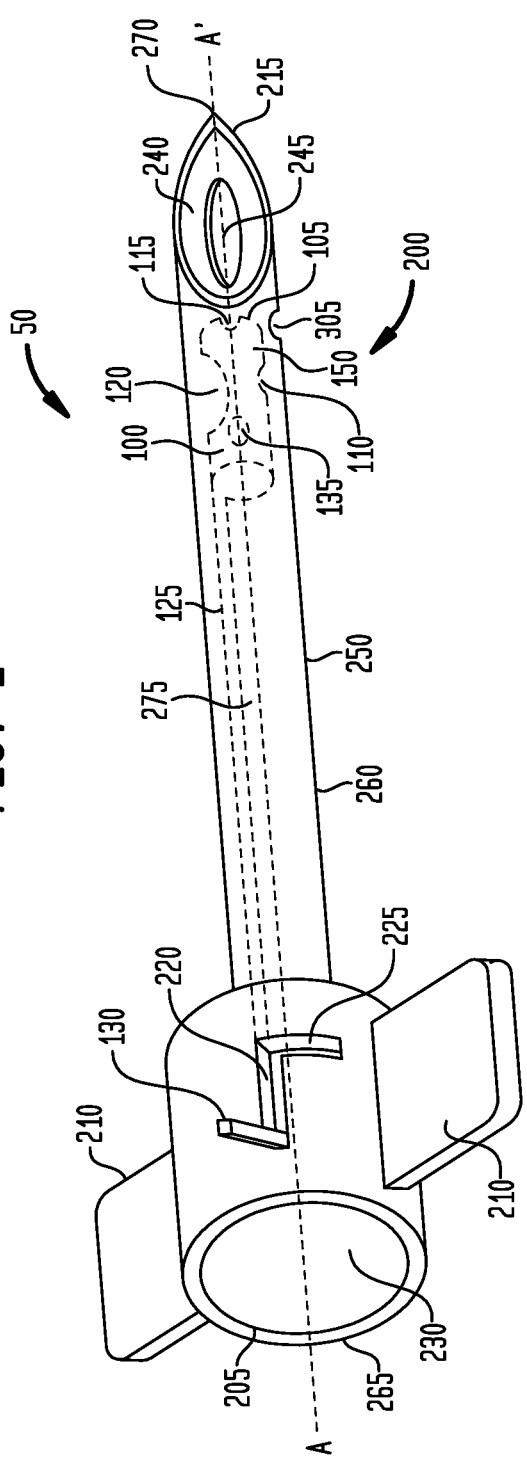
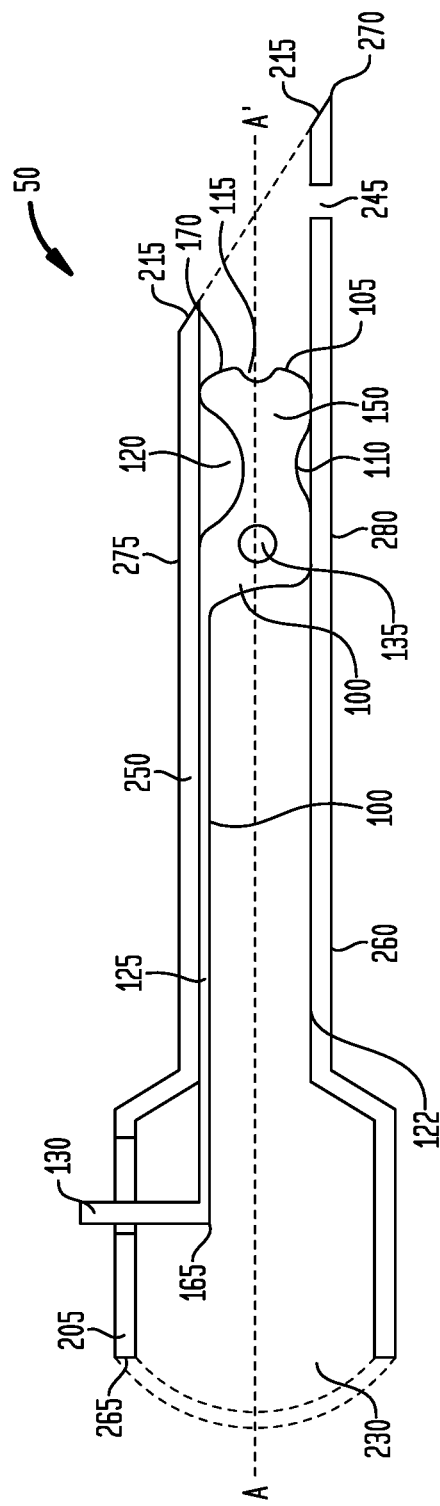

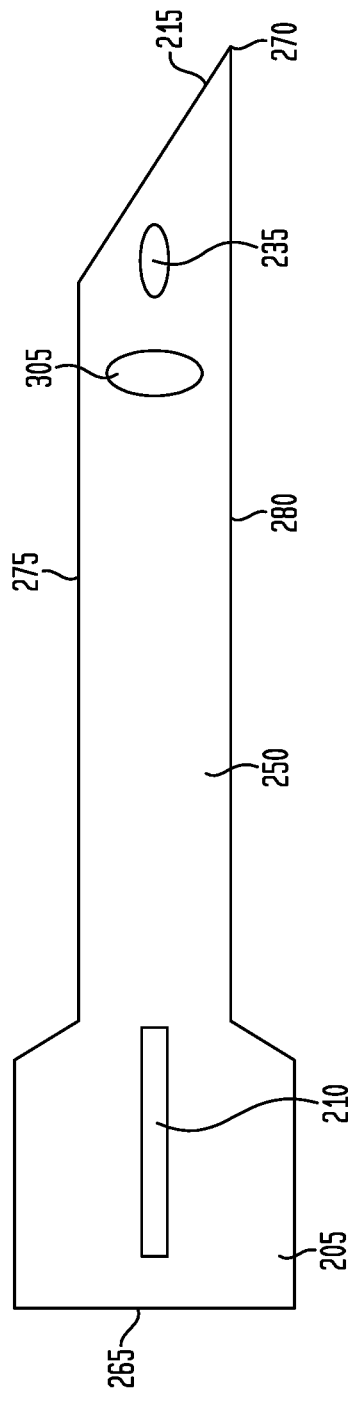
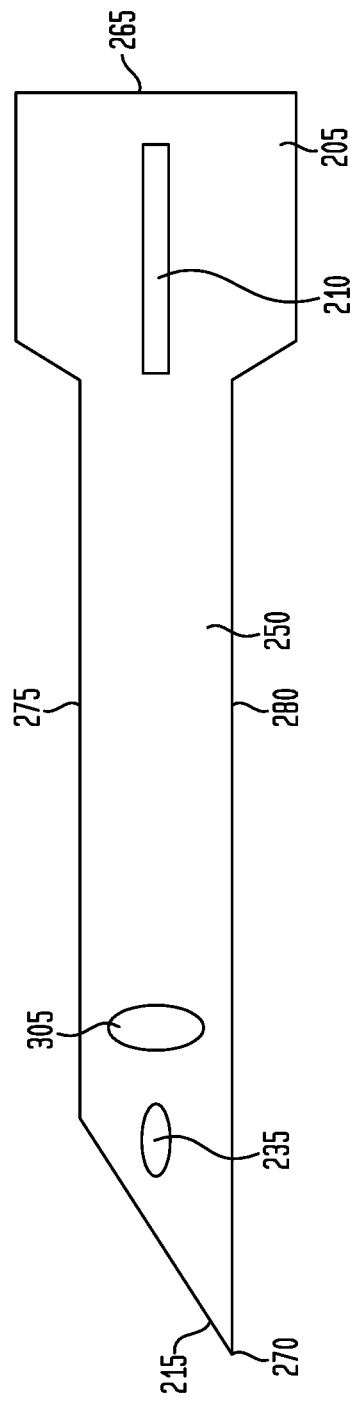

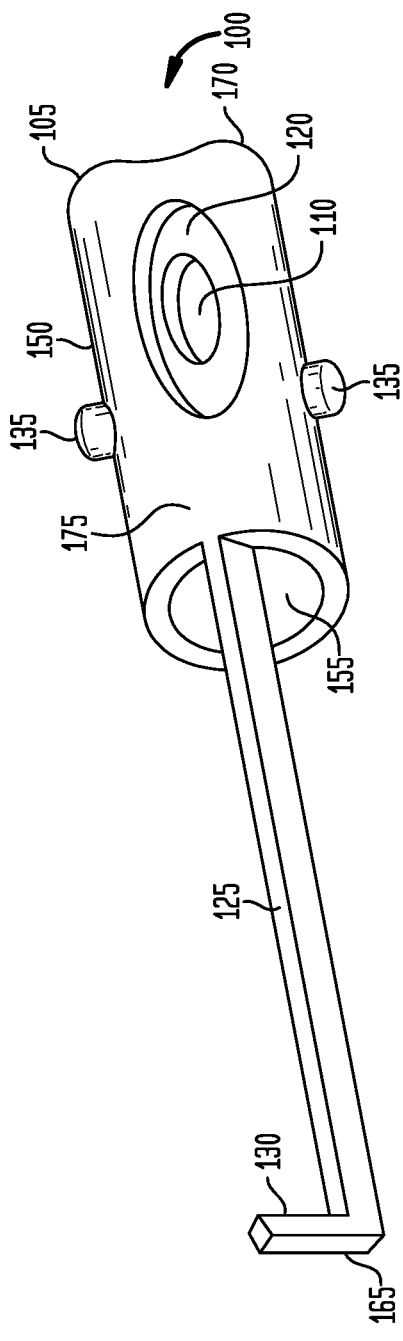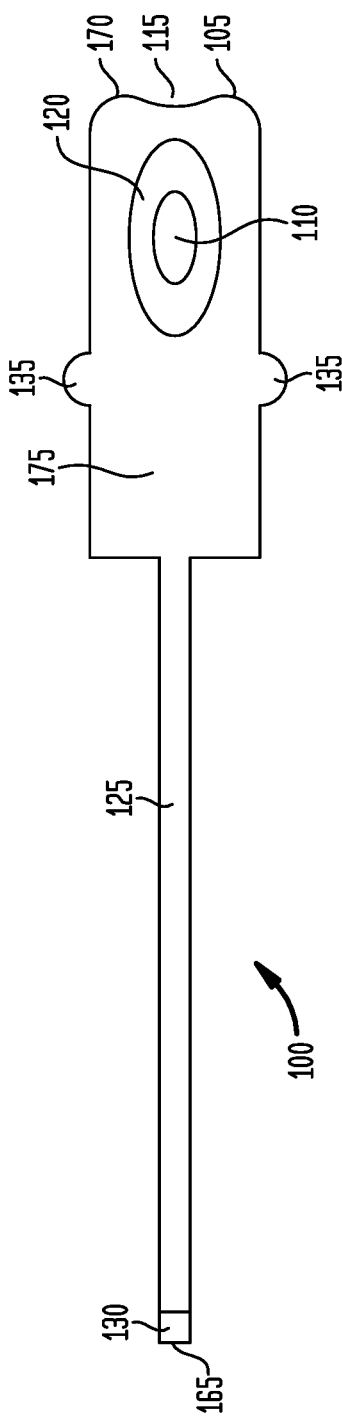

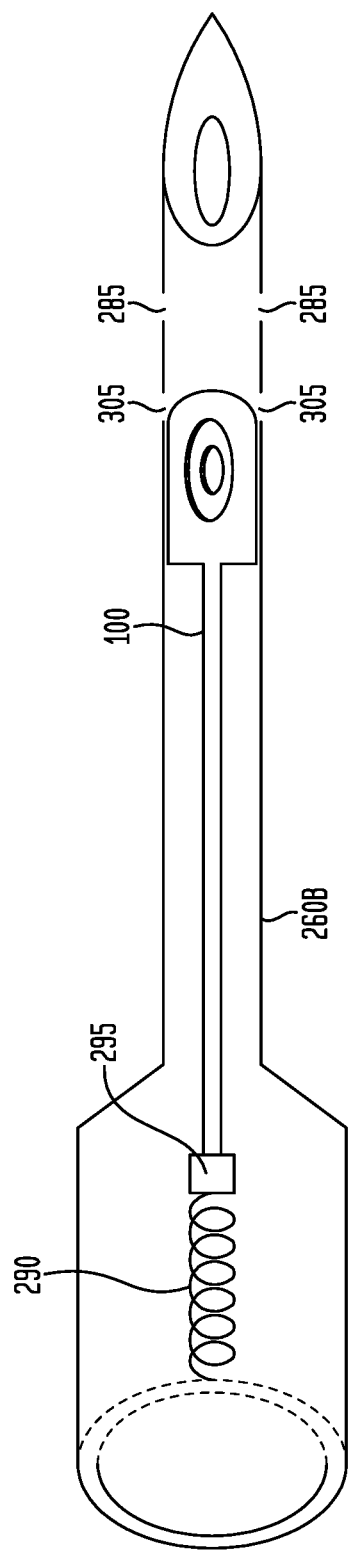

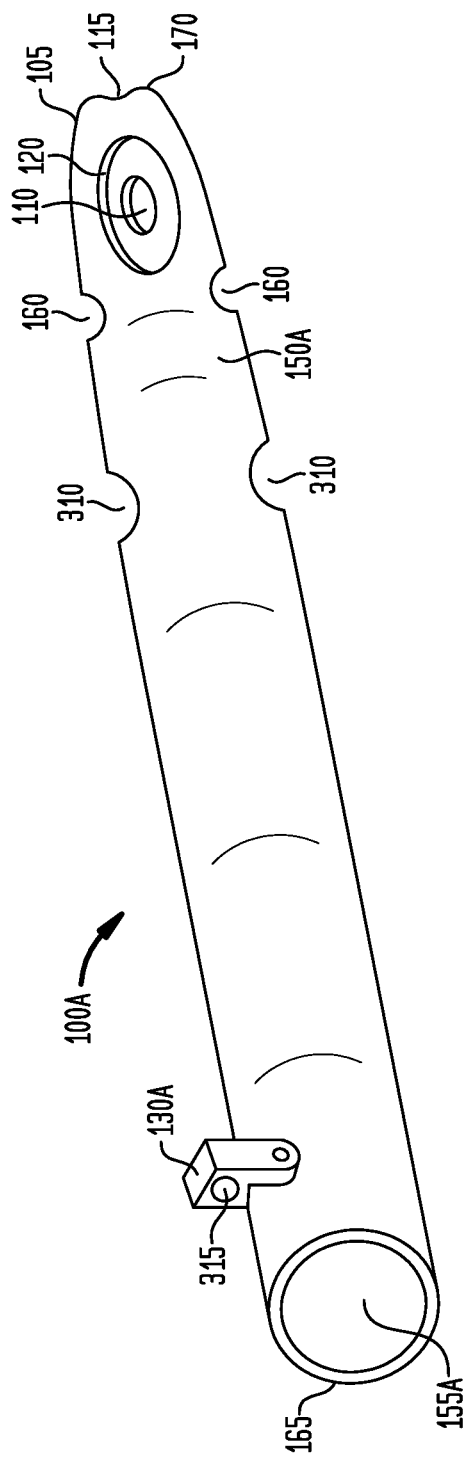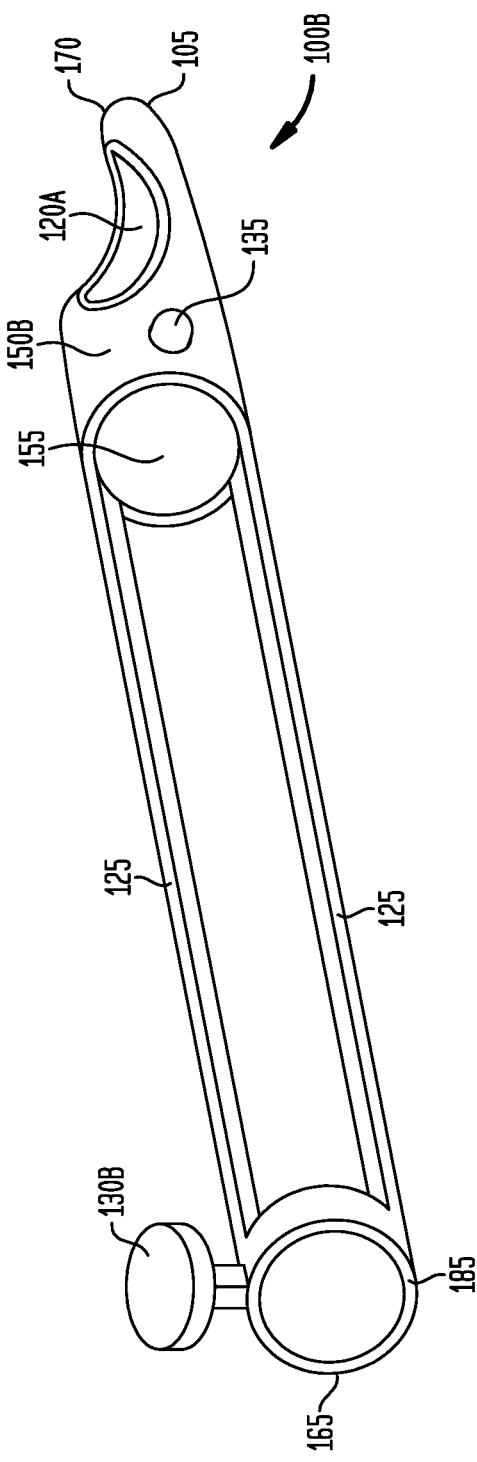

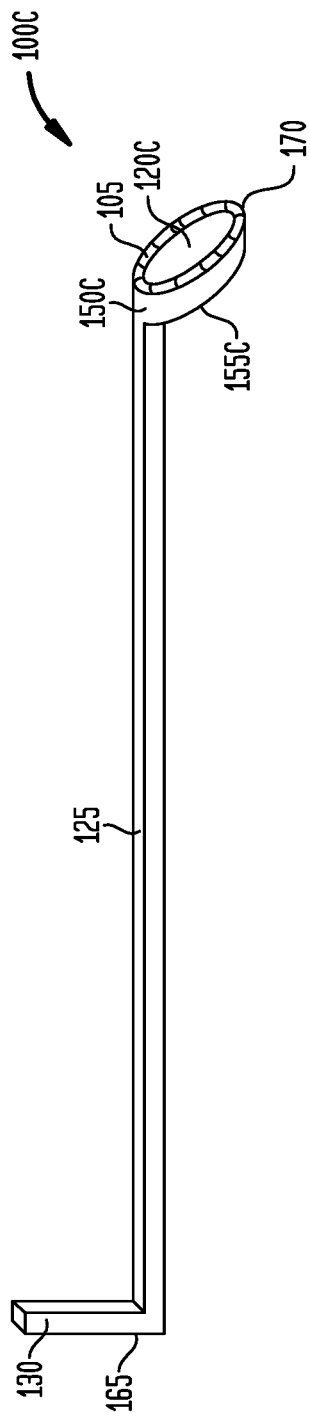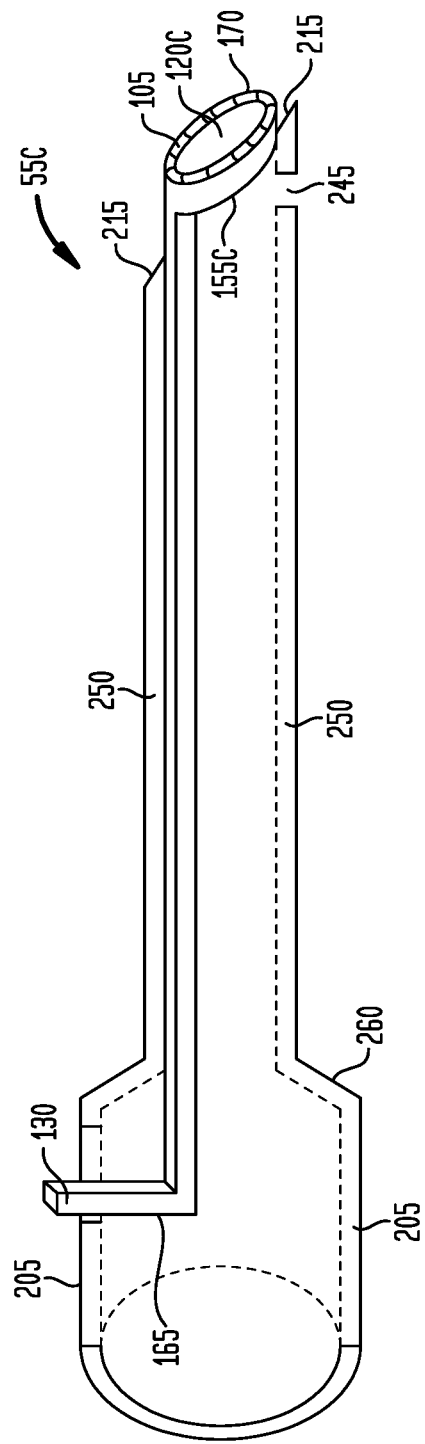

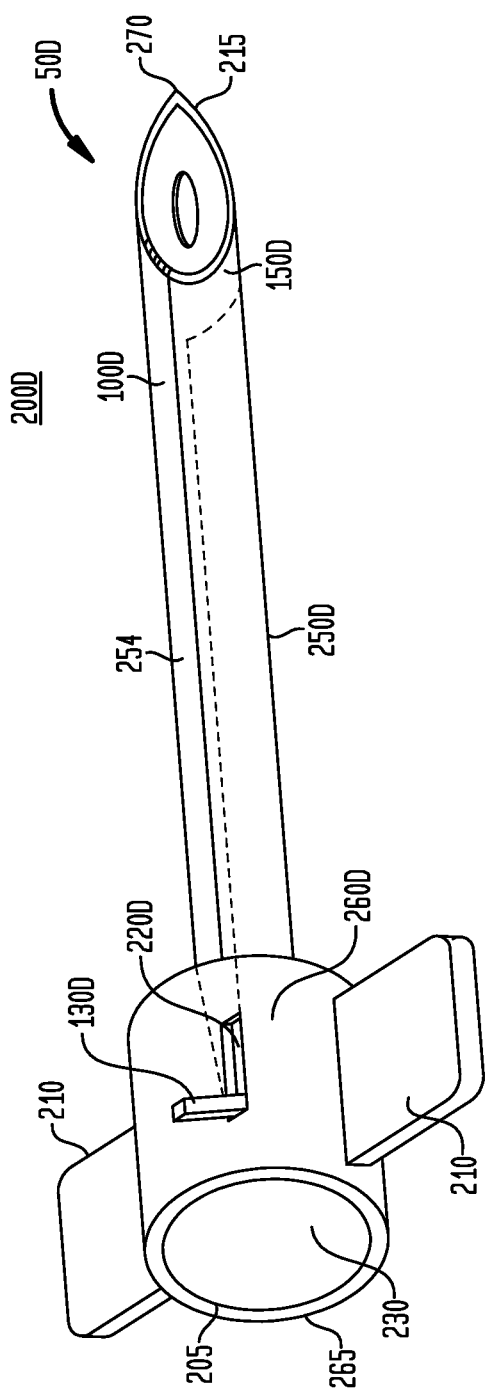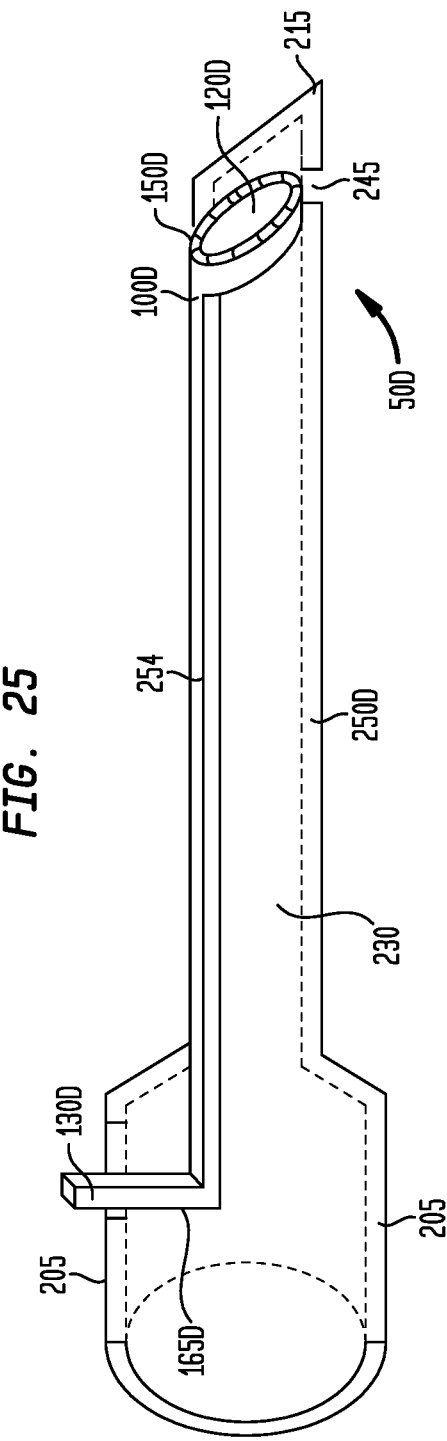

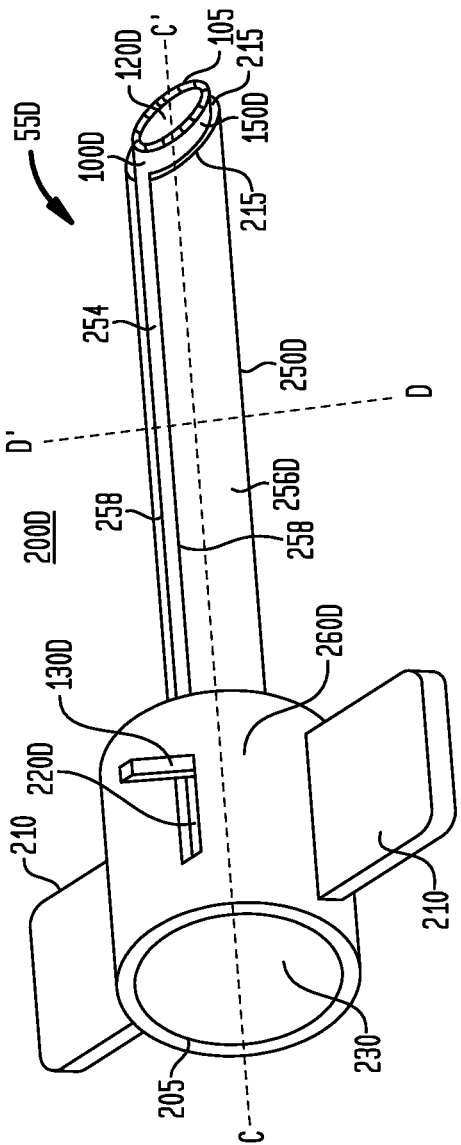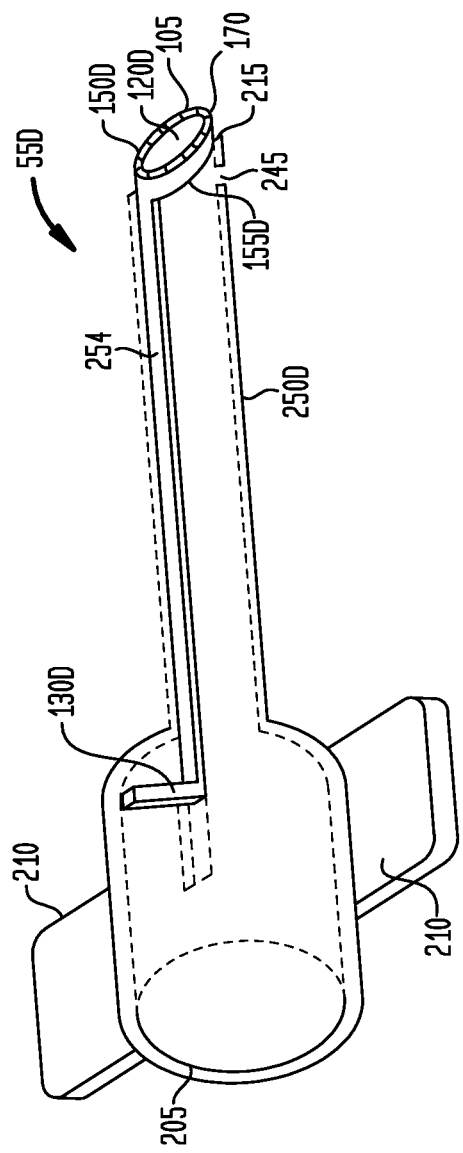

LOCKING HEMODIALYSIS NEEDLE ASSEMBLY WITH INTEGRAL NEEDLE TIP PROTECTOR

CROSS-REFERENCE TO A RELATED APPLICATION

This application is a continuation of and claims priority to and the benefit of U.S. patent application Ser. No. 16/792,385, filed Feb. 17, 2020, inventor Khaled Boubes, titled "Locking Hemodialysis Needle Assembly with Integral Needle Tip Protector", which is a nonprovisional of and claims the benefit of and priority to U.S. Provisional Patent Application No. 62/808,331, filed Feb. 21, 2019, inventor Khaled Boubes, titled "Locking Hemodialysis Needle Assembly with Integral Needle Tip Protector", and all of which are hereby incorporated herein by reference in their entireties with the same full force and effect as if set forth in their entireties herein.

FIELD OF THE INVENTION

The present invention, in general, relates to hemodialysis needles and, more specifically, relates to a hemodialysis needle assembly having an integral needle tip protector.

BACKGROUND OF THE INVENTION

Many hemodialysis patients have a surgically constructed fistula or graft connecting an artery and a vein, typically in one of the patient's arms, as a radiocephalic arteriovenous fistula. Generally, two hemodialysis needles are inserted into this fistula or graft for a hemodialysis session, one hemodialysis needle to remove blood from the patient for hemodialysis, and the other hemodialysis needle to return the blood to the patient from the hemodialysis machine.

Hemodialysis sessions may last for an extended period of time, generally several hours per session. In addition, hemodialysis needles are generally comparatively large, on the order of 15, 16 or 17 gauge, and are comparatively structurally stiff and inflexible to allow for higher flow rates (compared to more typical intravenous (IV) flow rates), typically on the order of 400-500 ml per minute.

During these extended hemodialysis sessions, the sharp needle point of these comparatively large and structurally inflexible hemodialysis needles is maintained within the lumen of the fistula or graft. As the patient moves, or as the hemodialysis needle may be perturbed, the sharp needle point may puncture the fistula or graft, create a hemorrhage and possibly also cause fistula thrombosis. This occurs in approximately 26% of hemodialysis patients, at an annual rate of over 5%. When this happens, a central dialysis catheter must be utilized for dialysis, which requires surgical placement of the central catheter and increases other risks to the patient, including infections. Additional surgical procedures may also be required, to repair or replace the injured fistula or graft.

A need remains, therefore, for a hemodialysis needle which reduces the likelihood of puncturing the fistula or graft, causing a hemorrhage and possibly also causing a fistula thrombosis. Such a hemodialysis needle should be comparatively easy for medical personnel to insert into the lumen of the fistula or graft, and should also protect the medical personnel from exposure to the sharp needle when the hemodialysis needle is removed from the patient.

SUMMARY OF THE INVENTION

The exemplary or representative embodiments of the present invention provide numerous advantages. Various representative embodiments provide a hemodialysis needle assembly which reduces the likelihood of puncturing the fistula or graft, causing a hemorrhage and possibly also causing a fistula thrombosis. Such representative embodiments of a hemodialysis needle assembly are comparatively easy for medical personnel to insert into the lumen of the fistula or graft, and extend the integral needle tip protector from a first, retracted position or configuration into a second, extended arrangement, position or configuration, which covers or shields a sharp needle tip of an outer needle of the needle assembly, and also may be locked into place. The representative embodiments of a hemodialysis needle assembly further provide protection to the medical personnel from exposure to the sharp needle tip when the hemodialysis needle assembly is removed from the patient, as the integral needle tip protector remains in the second, locked and extended arrangement, position or configuration or remains locked in the second, locked and extended arrangement, position or configuration.

A needle assembly for medical or surgical use is disclosed, such as for hemodialysis. A representative embodiment of the needle assembly comprises an outer needle assembly and an integral needle tip protector. A representative embodiment of the outer needle assembly comprises: an outer needle comprising: a first lumen; a first aperture with a sharp needle tip at a first, distal end of the outer needle; and a second aperture arranged opposite the first aperture. The integral needle tip protector is arranged within the first lumen and moveable within the first lumen between a first retracted position or configuration and a second (locked) position or configuration. A representative embodiment of the integral needle tip protector comprises: a needle tip cover arranged to shield the sharp needle tip in the second (and/or locked) position or configuration, the needle tip cover comprising: a smooth or beveled distal surface forming a blunt tip; a first opening aligned with the first aperture in the second position or configuration; and a second opening aligned with the second aperture in the second position or configuration.

In a representative embodiment, the needle tip cover may further comprise: a third opening arranged in the blunt tip. In another representative embodiment, the outer needle assembly may further comprise: one or more third apertures arranged on one or more lateral sides of the outer needle assembly spaced apart from or proximal to the first and second apertures.

In a representative embodiment, the integral needle tip protector may further comprise: an actuator at a second, proximal end of the integral needle tip protector; and a connecting rod coupling the actuator to the needle tip cover.

In another representative embodiment, the actuator may further comprise a recess or a detent; and the outer needle assembly may further comprise a mating detent or recess coupleable to the recess or detent of the actuator.

Also in a representative embodiment, the outer needle assembly may further comprise: a connector coupled to a second, proximal end of the outer needle to couple the outer needle to a syringe or tubing. In a representative embodiment, the outer needle assembly may further comprise: one or more handles coupled to the connector.

In a representative embodiment, the connector further comprises: a first longitudinal channel; and a second transverse channel. In such a representative embodiment, the actuator is moveable within the first longitudinal channel to move the integral needle tip protector from the first retracted configuration to the second position or configuration, and the actuator is moveable within the second transverse channel to lock the integral needle tip protector in the second position or configuration.

In a representative embodiment, in the second position or configuration, the needle tip cover extends longitudinally over the over the sharp needle tip at the first distal end of the outer needle. Also in a representative embodiment, the needle tip cover is substantially cylindrical and further comprises a second lumen, and the needle tip cover substantially abuts the first lumen.

Also in a representative embodiment, the needle tip cover may further comprise: one or more detents arranged on one or more lateral sides of the needle tip cover, each of the one or more detents having a smooth surface; and the outer needle may further comprise: one or more mating recesses arranged on one or more lateral sides of the outer needle to couple to the one or more detents in the second (or locked) position or configuration. Alternatively, in another representative embodiment, the outer needle may further comprise: one or more detents arranged on one or more lateral sides of the outer needle and extending within the lumen; and the needle tip cover may further comprise: one or more mating recesses arranged on one or more lateral sides of the needle tip cover to couple to the one or more detents in the second (or locked) position or configuration.

In a representative embodiment, the second opening may be substantially congruent with the second aperture, and the first opening may be at least partially congruent with the first aperture.

In another representative embodiment, the outer needle assembly may further comprise: a spring coupled to the integral needle tip protector; and an actuator to release the spring to move the integral needle tip protector from the first retracted configuration to the second (or locked) position or configuration.

In another representative embodiment, the integral needle tip protector may further comprise: a connecting ring; an actuator coupled to the connecting ring at a proximal end of the integral needle tip protector; and a plurality of connecting rods coupling the connecting ring to the needle tip cover.

In another representative embodiment, a needle assembly also comprises an outer needle assembly and an integral needle tip protector. A representative embodiment of the outer needle assembly comprises: an outer needle comprising: a first lumen; a first aperture with a sharp needle tip at a first, distal end of the outer needle; and a second aperture arranged opposite the first aperture; and the outer needle assembly further comprising a connector coupled to a proximal end of the outer needle, the connector having a first longitudinal channel and a second transverse channel. The integral needle tip protector is arranged within the first lumen and moveable within the first lumen between a first retracted position or configuration and a second (or locked) position or configuration. A representative embodiment of the integral needle tip protector comprises: a needle tip cover arranged to shield the sharp needle tip in the second (or locked) position or configuration, the needle tip cover comprising: a smooth or beveled distal surface forming a blunt tip; a first opening aligned with the first aperture in the second (or locked) position or configuration; and a second opening aligned with the second aperture in the second (or locked) position or configuration; a third opening arranged in the blunt tip; and with the representative embodiment of the integral needle tip protector further comprising an actuator at a second, proximal end of the integral needle tip protector; and a connecting rod coupling the actuator to the needle tip cover.

In another representative embodiment, the outer needle further comprises a longitudinal slot, and the integral needle tip protector further comprises a sliding connector coupled to the needle tip cover, the sliding connector slideable within the longitudinal slot.

In another representative embodiment, a needle assembly is disclosed for medical or surgical use, the needle assembly comprising: an outer needle assembly comprising: an outer needle comprising: a first lumen; a first aperture with a sharp needle tip at a first end of the outer needle; a second aperture arranged opposite the first aperture; a longitudinal slot; and a connector coupled to a second end of the outer needle, the connector having a first longitudinal channel; and an integral needle tip protector arranged within the first lumen and moveable within the first lumen between a first retracted configuration and a second extended configuration, the integral needle tip protector comprising: a needle tip cover arranged at a first end of the integral needle tip protector to shield the sharp needle tip in the second extended configuration, the needle tip cover comprising a smooth or beveled distal surface; an actuator at a second end of the integral needle tip protector; and a sliding connector coupling the actuator to the needle tip cover, the sliding connector slidable in the longitudinal slot.

In a representative embodiment, the actuator is moveable within the first longitudinal channel to slide the sliding connector in the longitudinal slot and move the integral needle tip protector from the first retracted configuration to the second extended configuration. In another representative embodiment, the longitudinal slot further comprises a plurality of edges, and wherein the sliding connector has a plurality of edges having mating surfaces.

In yet another representative embodiment, a needle assembly also comprises an outer needle assembly and an integral needle tip protector. A representative embodiment of the outer needle assembly comprises: an outer needle comprising: a first lumen; a first aperture with a sharp needle tip at a first distal end of the outer needle; a second aperture arranged opposite the first aperture; one or more third apertures arranged on one or more lateral sides of the outer needle assembly proximal to the first and second apertures; one or more recesses arranged on one or more lateral sides of the outer needle; and the outer needle assembly further comprising a connector coupled to a proximal end of the outer needle, the connector having a first longitudinal channel and a second transverse channel. The integral needle tip protector is also arranged within the first lumen and moveable within the first lumen between a first retracted position or configuration and a second (or locked) position or configuration. A representative embodiment of the integral needle tip protector comprises: a needle tip cover arranged to shield the sharp needle tip in the second (or locked) position or configuration, the needle tip cover comprising: a smooth or beveled distal surface forming a blunt tip; a first opening aligned with the first aperture in the second (or locked) position or configuration; and a second opening aligned with the second aperture in the second (or locked) position or configuration; a third opening arranged in the blunt tip; one or more mating detents arranged on one or more lateral sides of the needle tip cover, each of the one or more detents having a smooth surface and coupleable to the one or more recesses of the outer needle in the second locked configuration; and with the representative embodiment of the integral needle tip protector further comprising an actuator at a proximal end of the integral needle tip protector, the actuator moveable within the first longitudinal channel to move the integral needle tip protector from the first retracted position or configuration to the second position or configuration, and moveable within the second transverse channel to lock the integral needle tip protector in the second (or locked) position or configuration; and a connecting rod coupling the actuator to the needle tip cover.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which:

FIG. 1 is an isometric view illustrating a representative first embodiment of a hemodialysis needle assembly having a representative first embodiment of an outer needle assembly and a representative first embodiment of an integral needle tip protector in a first, retracted arrangement, position or configuration.

FIG. 2 is an elevational (side), cut-away view (in the A-A' plane) illustrating the representative first embodiment of the hemodialysis needle assembly having the representative first embodiment of the outer needle assembly and the representative first embodiment of the integral needle tip protector of FIG. 1 in the first, retracted arrangement, position or configuration.

FIG. 7 is a first side (or elevational) view illustrating the representative first embodiment of an outer needle assembly for a hemodialysis needle assembly.

FIG. 8 is a second side (or elevational) view illustrating the representative first embodiment of an outer needle assembly for a hemodialysis needle assembly.

FIG. 9 is a first isometric view illustrating the representative first embodiment of the integral needle tip protector.

FIG. 10 is plan, top view illustrating the representative first embodiment of the integral needle tip protector.

FIG. 17 is an top, plan cut-away view illustrating a representative third embodiment of an outer needle assembly for a hemodialysis needle assembly.

FIG. 18 is an isometric view illustrating a representative second embodiment of an integral needle tip protector.

FIG. 19 is an isometric view illustrating a representative third embodiment of an integral needle tip protector.

FIG. 22 is an isometric view illustrating a representative fourth embodiment of an integral needle tip protector.

FIG. 23 is an isometric cut-away view illustrating a representative second embodiment of the hemodialysis needle assembly having the representative first embodiment of the outer needle assembly and the representative fourth embodiment of the integral needle tip protector in a second (or locked) and extended arrangement, position or configuration.

FIG. 24 is an isometric view illustrating a representative third embodiment of a hemodialysis needle assembly having a representative fourth embodiment of an outer needle assembly and a representative fifth embodiment of an integral needle tip protector in a first, retracted arrangement, position or configuration.

FIG. 25 is an elevational (side), cut-away view illustrating the representative third embodiment of the hemodialysis needle assembly having the representative fourth embodiment of the outer needle assembly and the representative fifth embodiment of the integral needle tip protector of FIG. 24 in the first, retracted arrangement, position or configuration.

FIG. 26 is an isometric view illustrating the representative third embodiment of the hemodialysis needle assembly having the representative fourth embodiment of the outer needle assembly and the representative fifth embodiment of the integral needle tip protector in the second, extended arrangement, position or configuration.

FIG. 27 is an isometric, cut-away view illustrating the representative third embodiment of the hemodialysis needle assembly (of FIG. 26) having the representative fourth embodiment of the outer needle assembly and the representative fifth embodiment of the integral needle tip protector in the second, extended arrangement, position or configuration.

DETAILED DESCRIPTION OF REPRESENTATIVE EMBODIMENTS

Figure 3:
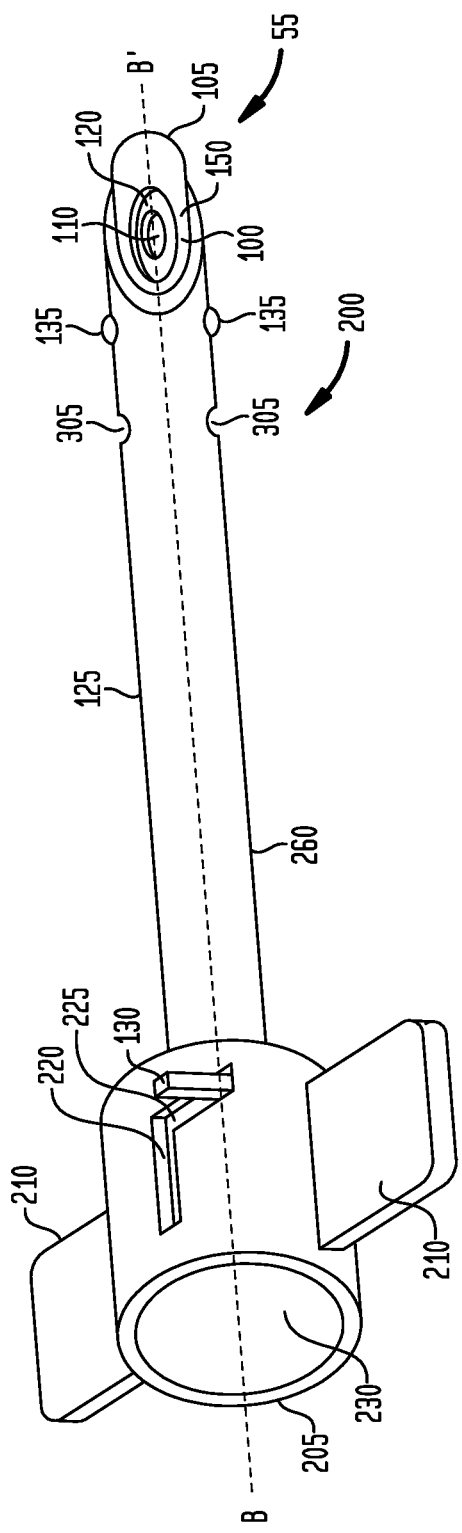
FIG. 3 is an isometric view illustrating the representative first embodiment of the hemodialysis needle assembly having the representative first embodiment of the outer needle assembly and the representative first embodiment of the integral needle tip protector in the second, locked and extended arrangement, position or configuration.

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

As mentioned above, various representative embodiments provide a hemodialysis needle assembly which reduces the likelihood of puncturing the fistula or graft, causing a hemorrhage and possibly also causing a fistula thrombosis. Such representative embodiments of a hemodialysis needle assembly are comparatively easy for medical personnel to insert into the lumen of the fistula or graft, and further provide protection to the medical personnel from exposure to the sharp needle when the hemodialysis needle assembly is removed from the patient.

Figure 4:
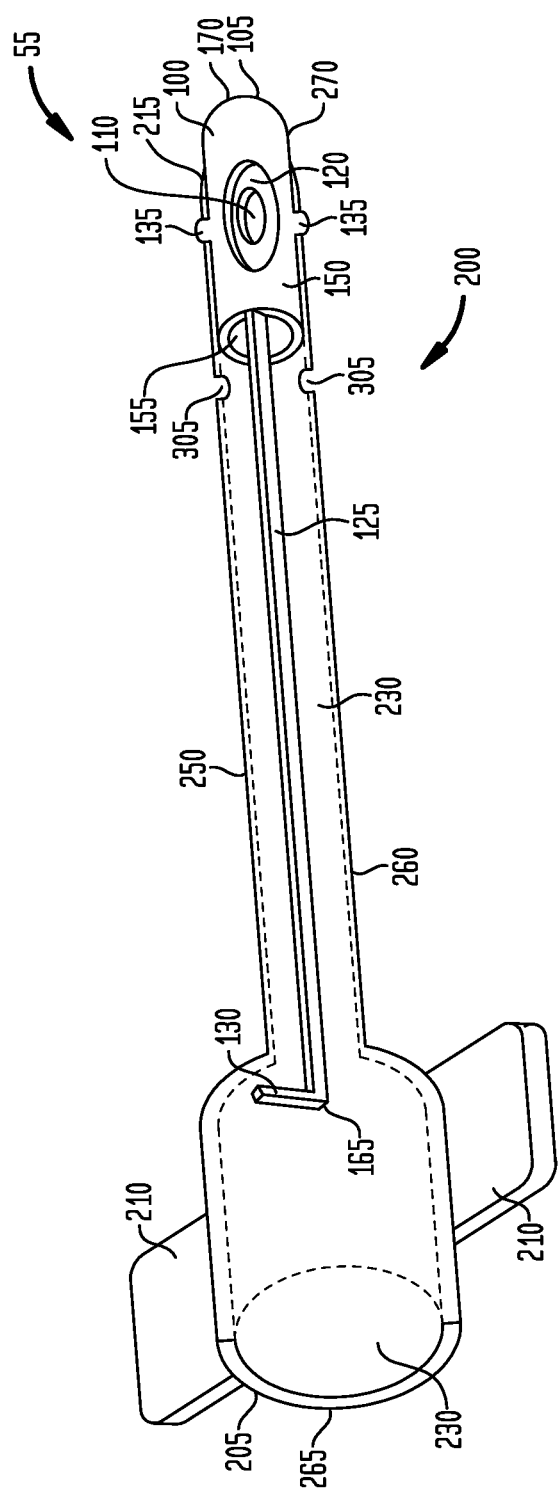
FIG. 4 is an isometric cut-away view illustrating the representative first embodiment of the hemodialysis needle assembly of FIG. 3 having the representative first embodiment of the outer needle assembly and the representative first embodiment of the integral needle tip protector in a second, locked and extended arrangement, position or configuration.
Figure 5:
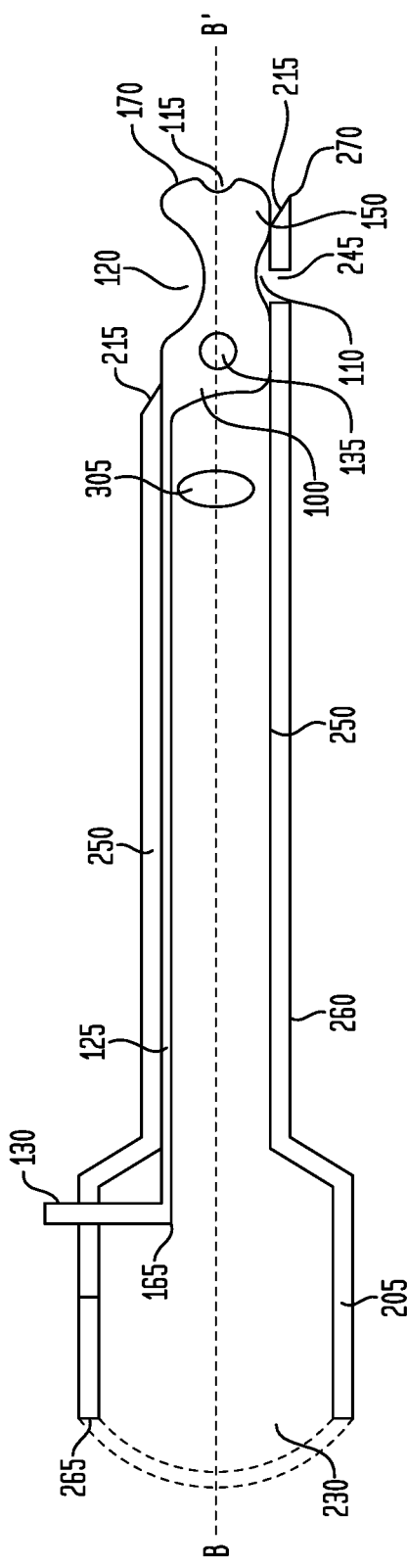
FIG. 5 is an elevational (side), cut-away view (in the B-B' plane) illustrating the representative first embodiment of the hemodialysis needle assembly having the representative first embodiment of the outer needle assembly and the representative first embodiment of the integral needle tip protector in the second, locked and extended arrangement or configuration of FIG. 3.
Figure 6:
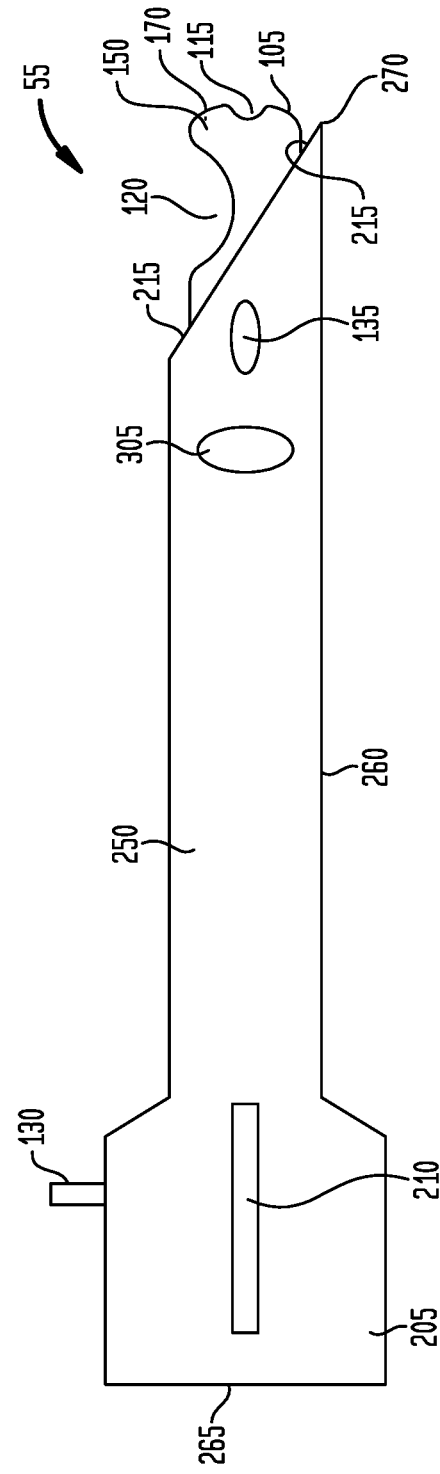
FIG. 6 is a side (or elevational) view illustrating the representative first embodiment of the hemodialysis needle assembly having the representative first embodiment of the outer needle assembly and the representative first embodiment of the integral needle tip protector in the second, locked and extended arrangement or configuration.

FIG. 1 is an isometric view illustrating a representative first embodiment of a hemodialysis needle assembly 200 having a representative first embodiment of an outer needle assembly 260 and a representative first embodiment of an integral needle tip protector 100 in a first, retracted arrangement, position or configuration 50. FIG. 2 is an elevational (side), cut-away (through the A-A' plane) illustrating the representative first embodiment of the hemodialysis needle assembly 200 having the representative first embodiment of the outer needle assembly 260 and the representative first embodiment of the integral needle tip protector 100 of FIG. 1 in the first, retracted arrangement, position or configuration 50. FIG. 3 is an isometric view illustrating the representative first embodiment of the hemodialysis needle assembly 200 having the representative first embodiment of the outer needle assembly 260 and the representative first embodiment of the integral needle tip protector 100 in the second, locked and extended arrangement, position or configuration 55. FIG. 4 is an isometric cut-away view illustrating the representative first embodiment of the hemodialysis needle assembly 200 of FIG. 3 having the representative first embodiment of the outer needle assembly 260 and the representative first embodiment of the integral needle tip protector 100 in a second, locked and extended arrangement, position or configuration 55. FIG. 5 is an elevational (side), cut-away (through the B-B' plane) illustrating the representative first embodiment of the hemodialysis needle assembly 200 having the representative first embodiment of the outer needle assembly 260 and the representative first embodiment of the integral needle tip protector 100 in the second, locked and extended arrangement, position or configuration 55 of FIG. 3. FIG. 6 is a side (or elevational) view illustrating the representative first embodiment of the hemodialysis needle assembly 200 having the representative first embodiment of the outer needle assembly 260 and the representative first embodiment of the integral needle tip protector 100 in the second, locked and extended arrangement, position or configuration 55. FIG. 7 is a first side (or elevational) view illustrating the representative first embodiment of an outer needle assembly 260 for a hemodialysis needle assembly 200. FIG. 8 is a second side (or elevational) view illustrating the representative first embodiment of an outer needle assembly 260 for a hemodialysis needle assembly 200.

While referred to as a hemodialysis needle assembly 200, those having skill in the art will recognize that that the hemodialysis needle assembly 200 may have many other medical and/or surgical uses and applications, in addition use for hemodialysis. Accordingly, the hemodialysis needle assembly 200 may simply be referred to as a needle assembly 200, and any reference to a needle assembly 200 should be understood to mean and include a hemodialysis needle assembly 200, and vice-versa. Stated another way, the needle assembly 200 of the present disclosure is not limited to hemodialysis applications, but may be utilized for any relevant medical or surgical application.

Referring to FIGS. 1-8, a representative embodiment of a hemodialysis needle assembly 200 comprises an outer needle assembly 260 and an integral needle tip protector 100 arranged within the first lumen 230 of the outer needle assembly 260. The outer needle assembly 260 comprises a hollow, tubular outer needle 250 having a sharp needle tip (or point) 215 at its first, distal end 270 used to puncture a patient's skin and fistula or graft for insertion of the outer needle 250 into the lumen of the fistula or graft. In a representative embodiment, for more laminar blood or other fluid flow, the integral needle tip protector 100 is typically abutting portions of the inner tubular walls 122 of the outer needle 250 within the first lumen 230. The outer needle 250 is typically comprised of a biocompatible metal or metal alloy, such as steel or titanium, or any other suitable biocompatible material which is or becomes known in the medical arts. The integral needle tip protector 100 is typically comprised of a polymer or plastic, as described in greater detail below, but also may be comprised of a biocompatible metal or metal alloy, such as steel or titanium, or any other suitable biocompatible material which is or becomes known in the medical arts.

The outer needle 250 has a sharp first aperture (opening, inlet or outlet) 240 extending obliquely from a superior or top side 275 to the first, distal end 270 and forming the sharp needle tip 215, and further has a second (typically blunt or otherwise not sharp) aperture (opening, inlet or outlet) 245 on an inferior or bottom side 280 of the outer needle 250 opposite the first aperture 240, as illustrated. For ease of reference, these first, second and other (third, fourth) openings in the outer needle 250 are referred to as apertures, in this instance first and second apertures 240, 245, to distinguish them from corresponding openings (holes, inlets or outlets) in the integral needle tip protector 100, discussed in greater detail below.

The outer needle assembly 260 further comprises a connector 205 (at a second, proximal end 265), such as for connecting to a syringe or tubing, and typically also comprises handles 210, for medical personnel to grasp when inserting or removing the hemodialysis needle assembly 200 into or from the patient. As illustrated, in a representative embodiment, the outer needle assembly 260 also comprises a first longitudinal channel 220, generally arranged within the connector 205 (although it could have other locations, depending on the selected embodiment), utilized for movement and positioning of the integral needle tip protector 100 from the first, retracted arrangement, position or configuration to the second, locked and extended arrangement or configuration, and a second, transverse channel 225, utilized to lock or maintain the integral needle tip protector 100 in the second, locked and extended arrangement, position or configuration.

As an option, the outer needle assembly 260 also comprises one or more third apertures (openings, holes, inlets or outlets) 305 arranged or located on opposite lateral sides of the outer needle 250, spaced apart from (proximally) the first and second apertures 240, 245, and also proximal to the needle tip cover 150 when the integral needle tip protector 100 is in the second, locked and extended arrangement or configuration, as illustrated. The one or more third apertures 305 thereby allow for additional blood or other fluid flow through the first lumen 230 when the integral needle tip protector 100 is in the second, locked and extended arrangement or configuration. Alternatively, the one or more third apertures (openings, holes, inlets or outlets) 305 may be arranged instead in other locations, such as on top (upper) and bottom (lower) sides 275, 280 of the outer needle 250, also spaced apart from (proximally) the first and second apertures 240, 245, and also spaced apart from (proximally) the needle tip cover 150 when the integral needle tip protector 100 is in the second, locked and extended arrangement or configuration.

The outer needle assembly 260 also comprises one or more mating (fourth) apertures (openings, holes or recesses) 235, such as on opposite lateral sides of the outer needle 250 in a representative embodiment, which are utilized with mating detents (smooth retaining or locking extensions or protrusions) 135 of the integral needle tip protector 100 to provide additional locking in the second, locked and extended arrangement or configuration, as discussed in greater detail below.

For ease of reference, directions and orientations utilized herein are with reference to the lengthwise axis of the outer needle 250, as the longitudinal dimension, with the radial dimension extending radially (or outwards) from the lengthwise axis of the outer needle 250, and with the transverse dimension extending orthogonally to the longitudinal dimension, e.g., across the width of the outer needle 250, as will be apparent to those having skill in the art from the following disclosure, for example, the transverse dimension being east or west to a north-south longitudinal dimension.

In the first, retracted arrangement, position or configuration, the integral needle tip protector 100 (illustrated using dashed lines in FIG. 1) is not exposed but is maintained mostly or entirely within the first lumen 230 of the outer needle assembly 260 (except for the actuator 130, as discussed in greater detail below). In the second, locked and extended arrangement, position or configuration, the integral needle tip protector 100 is partially within the first lumen 230 of the outer needle assembly 260 but now extends in the longitudinal direction out of the first lumen 230, i.e., extends further from the distal end 270 of the outer needle assembly 260 as illustrated and shields, covers or blocks the sharp needle tip 215 of the outer needle 250.

Figure 11:
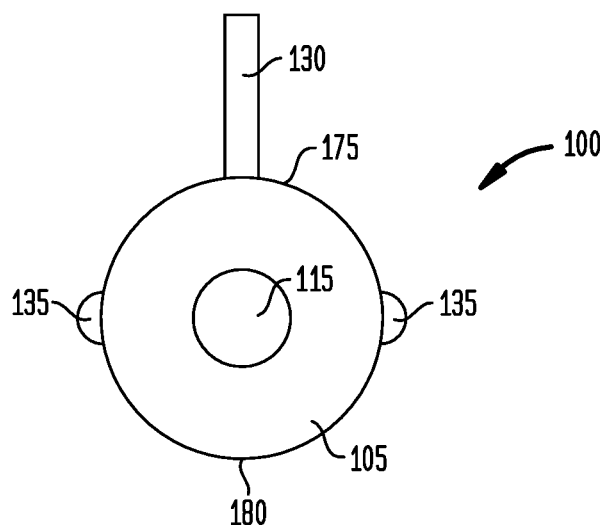
FIG. 11 is a front view illustrating the representative first embodiment of the integral needle tip protector.
Figure 12:
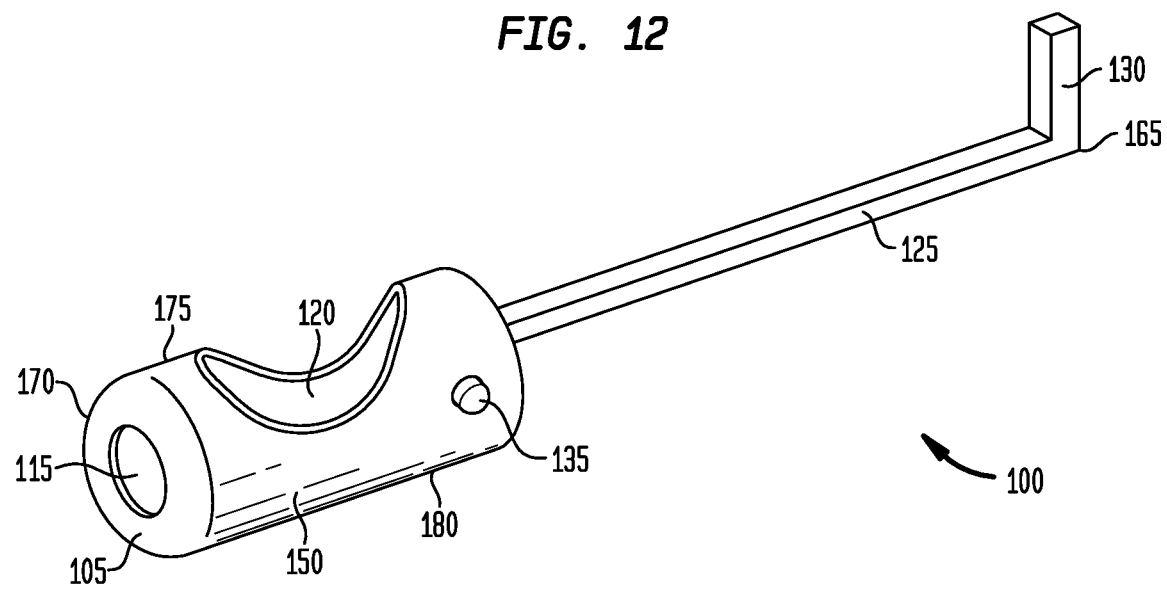
FIG. 12 is a second isometric view illustrating the representative first embodiment of the integral needle tip protector.
Figure 13:
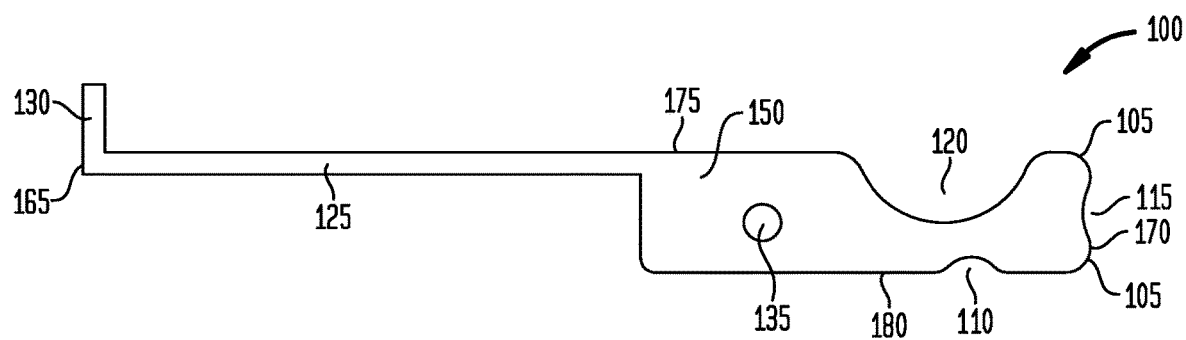
FIG. 13 is a first side (or elevational) view illustrating the representative first embodiment of the integral needle tip protector.
Figure 14:
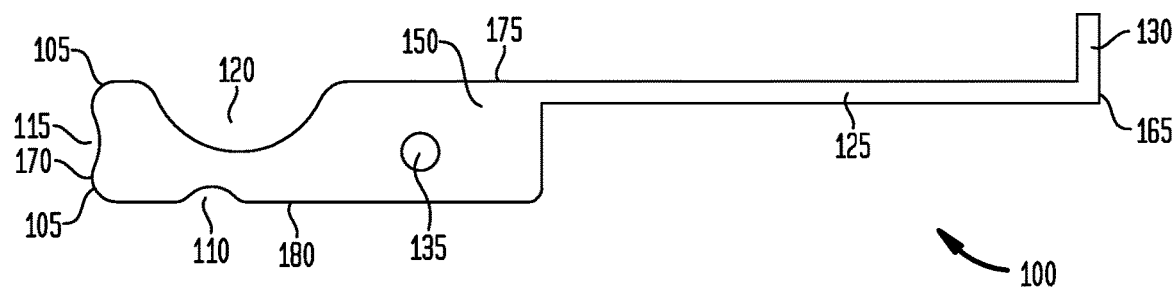
FIG. 14 is a second side (or elevational) view illustrating the representative first embodiment of the integral needle tip protector.
Figure 15:
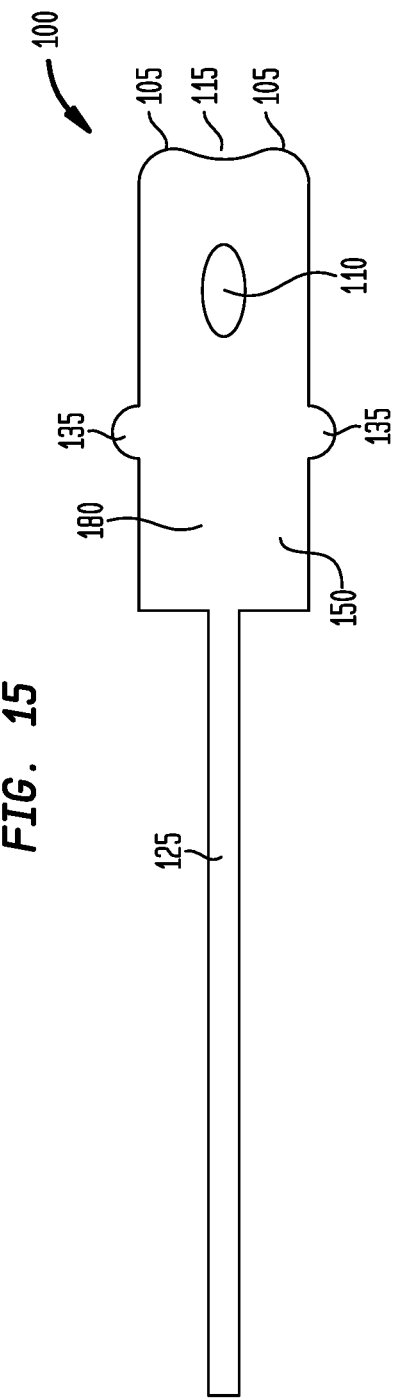
FIG. 15 is a plan, bottom view illustrating the representative first embodiment of the integral needle tip protector.

FIG. 9 is a first isometric view illustrating the representative first embodiment of the integral needle tip protector 100. FIG. 10 is plan, top view illustrating the representative first embodiment of the integral needle tip protector 100. FIG. 11 is a front view illustrating the representative first embodiment of the integral needle tip protector 100. FIG. 12 is a second isometric view illustrating the representative first embodiment of the integral needle tip protector 100. FIG. 13 is a first side view illustrating the representative first embodiment of the integral needle tip protector 100. FIG. 14 is a second side view illustrating the representative first embodiment of the integral needle tip protector 100. FIG. 15 is a plan, bottom view illustrating the representative first embodiment of the integral needle tip protector 100.

As illustrated in FIGS. 2, 3, 5 and 9-15, the representative first embodiment of the integral needle tip protector 100 comprises a needle tip cover 150 (and as illustrated, is configured, structured or shaped as a hollow, beveled cylinder or tube having a second lumen 155 and further having a smooth, curved or beveled surface 105), an actuator 130, and typically a connecting rod (connector or other coupling) 125 connecting the needle tip cover 150 to the actuator 130. The integral needle tip protector 100, comprising the needle tip cover 150, the connecting rod 125, and the actuator 130, is arranged within the first lumen 230 of the outer needle assembly 260, with the actuator 130 also extending radially through the channel 220 or 225 from the first lumen 230 within the outer needle assembly 260 to the exterior of the outer needle assembly 260. The actuator 130 is moveable within the first, longitudinal channel 220 and second, transverse channel 225 of the outer needle assembly 260.

During insertion of the outer needle 250 of the outer needle assembly 260 into the lumen of a fistula, graft or other vessel, the integral needle tip protector 100 is maintained in the first, retracted arrangement, position or configuration. Following insertion, the actuator 130 may be grasped by medical personnel and moved (pushed or slid) longitudinally along the first, longitudinal channel 220 to move the integral needle tip protector 100 from the first, retracted arrangement or configuration to the second, locked and extended arrangement or configuration, and then moved transversely along the second, transverse channel 225 to maintain or lock the integral needle tip protector 100 in the second, locked and extended arrangement or configuration. As mentioned above, in the second, locked and extended arrangement or configuration, the integral needle tip protector 100 is partially within the first lumen 230 of the outer needle assembly 260 but now extends in the longitudinal direction out of the first lumen 230, i.e., the needle tip cover 150 extends further from the distal end 270 of the outer needle assembly 260 as illustrated and covers or blocks the sharp needle tip 215 of the outer needle 250, protecting the lumen of a fistula, graft or other vessel from being punctured when a patient may move during dialysis, for example. Following dialysis, the integral needle tip protector 100 is maintained in the second, locked and extended arrangement or configuration when withdrawn from the lumen of a fistula, graft or other vessel, keeping the sharp needle tip 215 of the outer needle 250 covered by the needle tip cover 150 of the integral needle tip protector 100, thereby also protecting medical personnel from possible injury from the sharp needle tip 215.

The needle tip cover 150 comprises a first opening (aperture, hole, inlet or outlet) 120 on the superior or top side 175 of the integral needle tip protector 100, and a second opening (aperture, hole, inlet or outlet) 110 on the inferior or bottom side 180 of the integral needle tip protector 100. When the integral needle tip protector 100 has been positioned into the second, locked and extended arrangement or configuration: (1) the first opening 120 of the integral needle tip protector 100 is aligned with the first aperture 240 of the outer needle 250 (of the outer needle assembly 260); and (2) the second opening 110 of the integral needle tip protector 100 is aligned with the second aperture 245 of the outer needle 250 (of the outer needle assembly 260). The needle tip cover 150 is also hollow, having a second lumen 155. Accordingly, when the integral needle tip protector 100 has been positioned into the second, locked and extended arrangement or configuration, blood or other fluid is allowed to flow freely to or from the connector 205, through the first lumen 230 of the outer needle 250 and through the second lumen 155 of the needle tip cover 150, in or out of the first opening 120 and first aperture 240, in or out of the second opening 110 and second aperture 245, and in or out of the lumen of a fistula, graft or other vessel.

The needle tip cover 150 generally has a substantially smooth and curved or beveled surface 105, forming a blunt tip, as illustrated, creating this substantially puncture-resistant functionality. For example, the substantially smooth and curved or beveled surface 105 does not have a significant discontinuity, such as a sharp edge or point. The needle tip cover 150 may have any of myriad shapes, such as spherical, ellipsoid, curved, beveled, and so on, and several additional variations are illustrated and discussed below.

While the first opening 120 of the integral needle tip protector 100 is aligned (and may be at least partially congruent) with the first aperture 240 of the outer needle 250, in a representative embodiment, the first opening 120 is generally smaller in circumference than the first aperture 240, to block or cover (from within the first lumen 230) the sharp needle tip 215 (and/or sharp needle tip 215 edges) surrounding the first aperture 240 of the outer needle 250. Stated another way, in a representative embodiment, for the needle tip cover 150 to cover the sharp needle tip 215 surrounding the first aperture 240 of the outer needle 250, the needle tip cover 150 extends within the first lumen 230 and within the first aperture 240, such that the first opening 120 partially covers the first aperture 240 (illustrated in FIG. 21 and discussed in greater detail below). As the second aperture 245 of the outer needle 250 is not utilized for puncturing a vessel and is generally not sharp, in a representative embodiment, the second opening 110 is generally congruent with (or may have any shape) and may be the same size or larger than the second aperture 245 (illustrated in FIG. 20 and discussed in greater detail below).

Because of the potential of the potential for the first opening 120 to reduce the blood or fluid flow through the first aperture 240, in a representative embodiment, as an option, the needle tip cover 150 may further comprise a third opening (aperture, hole, inlet or outlet) 115 at the distal end 170 of the integral needle tip protector 100, allowing for additional blood or other fluid flow.

Also in a representative embodiment, as another option, the needle tip cover 150 typically further comprises one or more detents (or tabs) 135, such as arranged on one or more lateral sides of the needle tip cover 150 (or other suitable locations on the needle tip cover 150). Each of the one or more detents 135 are extensions or protrusions having a smooth or beveled surface (to avoid puncturing or abrasions within the lumen of the fistula or graft) and extend radially on the lateral sides of the needle tip cover 150, as illustrated. In the first, retracted arrangement or configuration, the detents 135 are compressed against the interior walls 122 of the outer needle 250. When the integral needle tip protector 100 is moved into the second, locked and extended arrangement or configuration, the detents are also moved into mating fourth apertures (openings, holes or recesses) 235 of the outer needle 250 (e.g., an interlocking or "snap fitting"). This interlocking provides additional locking functionality for the needle tip cover 150, in the event the needle tip cover 150 were to become disconnected from the connecting rod 125 or actuator 130 during use, preventing the needle tip cover 150 from being dislodged and entering the patient's bloodstream, and also helps maintain the integral needle tip protector 100 in the second, locked and extended arrangement or configuration during dialysis and further when the hemodialysis needle assembly 200 is removed from the patient. While illustrated with detents 135 in the needle tip cover 150 and mating fourth apertures (openings, holes or recesses) 235 in the outer needle 250, those having skill in the art will recognize that these structures may be reversed equivalently, with mating openings (holes or recesses) 160 provided in the needle tip cover 150 (as illustrated in FIG. 18) and detents 285 provided in the outer needle 250 and extending into the first lumen 230 (as illustrated in FIG. 16), and all such variations are considered equivalent and within the scope of the disclosure.

In a representative embodiment, the integral needle tip protector 100 is sized radially to fit within a first lumen 230 of an outer needle 250, such as a 15, 16 or 17 gauge needle. The needle tip cover 150 is also sized longitudinally to shield or cover the entire first aperture 240, which may be as long as 6 mm, for example and without limitation, such as the needle tip cover 150 having a length of 7-10 mm, also for example and without limitation.

Figure 16:
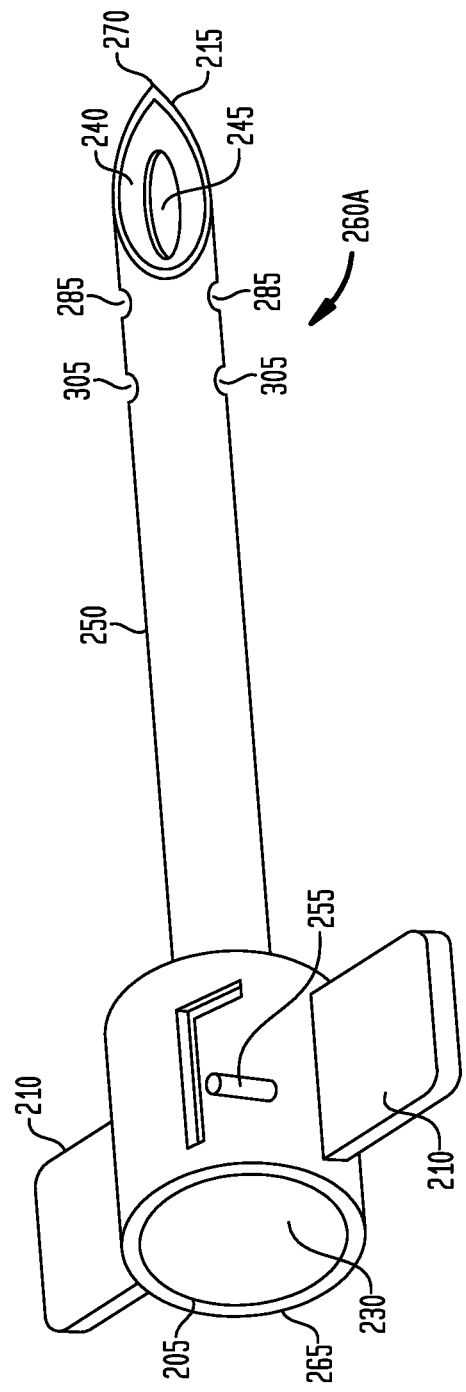
FIG. 16 is an isometric view illustrating a representative second embodiment of an outer needle assembly for a hemodialysis needle assembly.

FIG. 16 is an isometric view illustrating a representative second embodiment of an outer needle assembly 260A for a hemodialysis needle assembly 200. FIG. 17 is an isometric cut-away view illustrating a representative third embodiment of an outer needle assembly 260B for a hemodialysis needle assembly 200. FIG. 18 is an isometric view illustrating a representative second embodiment of an integral needle tip protector 100A. FIG. 19 is an isometric view illustrating a representative third embodiment of an integral needle tip protector 100B.

Referring to FIGS. 16 and 18, additional variations are illustrated, as outer needle assembly 260A and integral needle tip protector 100A. As illustrated, the representative second embodiment of an integral needle tip protector 100A has a hinged or pivoting actuator 130A, which includes a mating recess 315 for interlocking (snap fitting) with a detent 255 of the outer needle assembly 260A, as another locking mechanism. In addition, as mentioned above, for these representative embodiments, mating fourth openings (holes or recesses) 160 are provided in the needle tip cover 150A and detents 285 are provided in the outer needle 250 and extending into the first lumen 230. In addition, for the integral needle tip protector 100A, there is no separate connecting rod 125, and instead, the needle tip cover 150A extends longitudinally to the proximal end 165 of the integral needle tip protector 100A. As another variation, the distal end 170 of the needle tip cover 150A has a more ellipsoid shape, rather than a beveled cylinder illustrated in other Figures, as an example of any number of available variations, without limitation. In addition, for this embodiment, when optional one or more third apertures (openings, holes, inlets or outlets) 305 are included on opposite lateral sides of the outer needle 250, as discussed above, the integral needle tip protector 100A also includes one or more corresponding fifth openings (holes, inlets or outlets) 310 on opposite lateral sides of the integral needle tip protector 100A, as illustrated, which allow for additional blood or other fluid flow through the first lumen 230 when the integral needle tip protector 100A is in the second, locked and extended arrangement or configuration.

Referring to FIG. 17, the representative third embodiment of an outer needle assembly 260B is illustrated with an integral needle tip protector 100 in the first, retracted arrangement or configuration. As illustrated, that the outer needle assembly 260B may include a spring 290 (illustrated as a coil spring), with an actuator 295 utilized for releasing the spring 290 from a compressed state and moving the integral needle tip protector 100 into a second, locked and extended arrangement or configuration (not separately illustrated).

Referring to FIG. 19, the representative third embodiment of an integral needle tip protector 100B includes a plurality of connecting rods 125 coupling the needle tip cover 150B to a connecting ring 185, which in turn is coupled to an actuator 130B (configured as a button or button-like shape, as an available variation, for example and without limitation). The representative third embodiment of an integral needle tip protector 100B also illustrates the distal end 170 of the needle tip cover 150B having another, more "U" or cupped shape, rather than a beveled cylinder or ellipsoid illustrated in other Figures, also as an example of any number of available variations, without limitation.

Figure 20:
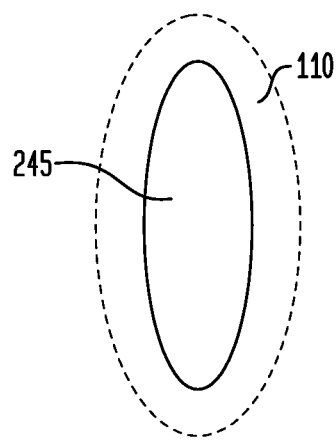
FIG. 20 is a plan view illustrating representative congruence of a second opening of the integral needle tip protector with the second aperture of the outer needle.

FIG. 20 is a plan, top view illustrating representative congruence of a second opening 110 of the needle tip cover 150 of the integral needle tip protector 100 with the second aperture 245 of the outer needle 250. As illustrated in FIG. 20, the second aperture 245 of the outer needle 250 is not utilized for puncturing a vessel and is generally not sharp, and in a representative embodiment, the second opening 110 (illustrated with dashed lines) is generally congruent with as illustrated (or may have any shape) and may be the same size or larger than the second aperture 245 (as illustrated).

Figure 21:
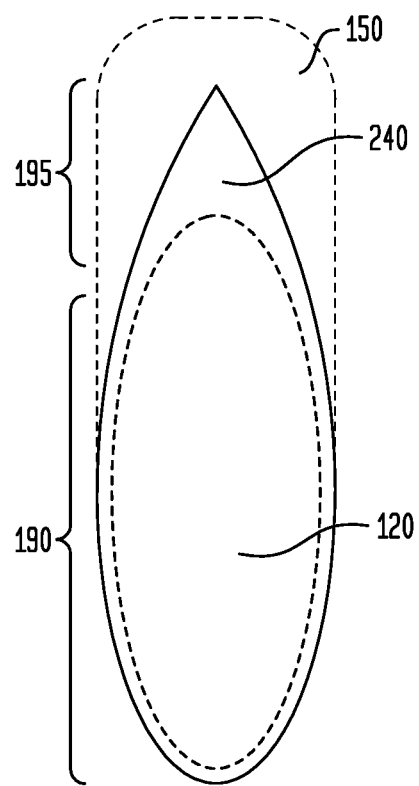
FIG. 21 is a plan view illustrating representative congruence of a first opening of the integral needle tip protector with the first aperture of the outer needle.

FIG. 21 is a plan, top view illustrating representative congruence of a first opening 120 of the needle tip cover 150 of the integral needle tip protector 100 with the first aperture 240 of the outer needle 250. As illustrated in FIG. 21, while the first opening 120 (illustrated with dotted lines) of the needle tip cover 150 (illustrated with dashed lines) of the integral needle tip protector 100 is aligned with the first aperture 240 (illustrated with solid lines) of the outer needle 250, in a representative embodiment, the first opening 120 is generally smaller in circumference than the first aperture 240, to block or cover (from within the first lumen 230) the sharp needle tip 215 (or sharp needle tip 215 edges) surrounding the first aperture 240 of the outer needle 250. Stated another way, in a representative embodiment, for the needle tip cover 150 to cover the sharp needle tip 215 surrounding the first aperture 240 of the outer needle 250, the needle tip cover 150 extends within the first lumen 230 and within the first aperture 240, such that the first opening 120 covers part of the first aperture 240, as illustrated. Also as illustrated, the first opening 120 of the needle tip cover 150 is partially congruent with the first aperture 240, in the region 190, and not congruent in region 195, to provide a cover for the sharp distal end 270 of the sharp needle tip 215.

FIG. 22 is an isometric view illustrating a representative fourth embodiment of an integral needle tip protector 100C. FIG. 23 is an isometric cut-away view illustrating a representative second embodiment of the hemodialysis needle assembly 200A having the representative first embodiment of the outer needle assembly 260 and the representative fourth embodiment of the integral needle tip protector 100C in a second (or locked) and extended arrangement, position or configuration 55C. Referring to FIGS. 22 and 23, additional variations are illustrated, as integral needle tip protector 100C. As illustrated, the representative fourth embodiment of the integral needle tip protector 100C also has an actuator 130, connecting rod 125, and a needle tip cover 150C, and operates as previously described for the hemodialysis needle assembly 200. For this embodiment, the needle tip cover 150C has a ring configuration, including a ring-shaped, smooth, curved or beveled surface 105. In addition, for this embodiment, depending upon the size (longitudinal dimension) of the needle tip cover 150C, there may be lateral space between the needle tip cover 150C and the sharp first aperture (opening, inlet or outlet) 240, also allowing for additional blood or other fluid flow through the first lumen 230 when the integral needle tip protector 100C is in the second, locked and extended arrangement, position or configuration 55C.

Figure 28:
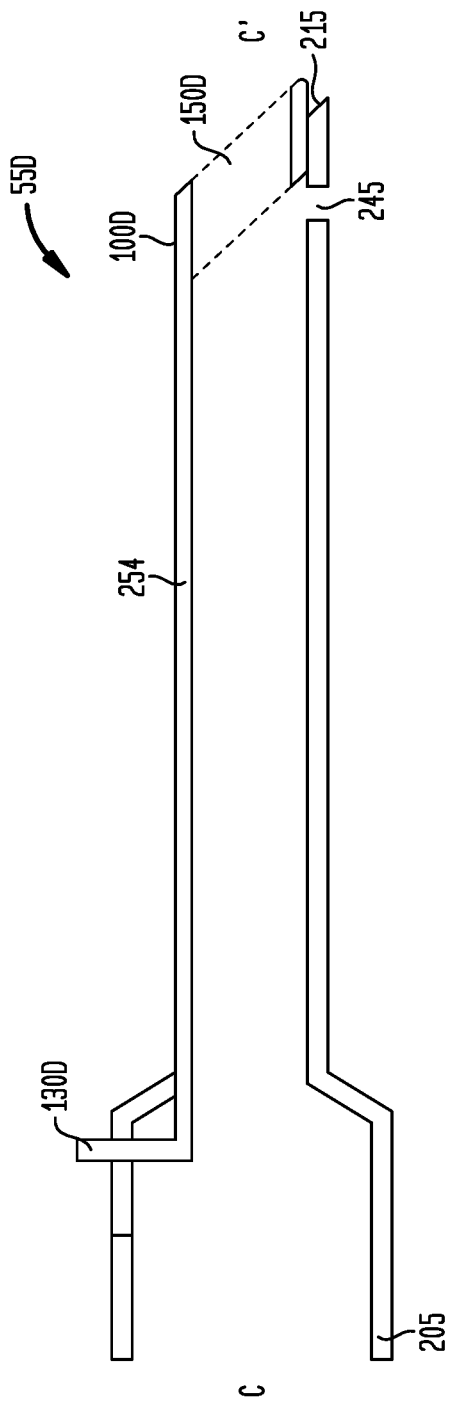
FIG. 28 is a cross-sectional view (through the C-C' plane) illustrating the representative third embodiment of the hemodialysis needle assembly (of FIG. 26) having the representative fourth embodiment of the outer needle assembly and the representative fifth embodiment of the integral needle tip protector in the second, extended arrangement, position or configuration.
Figure 29:
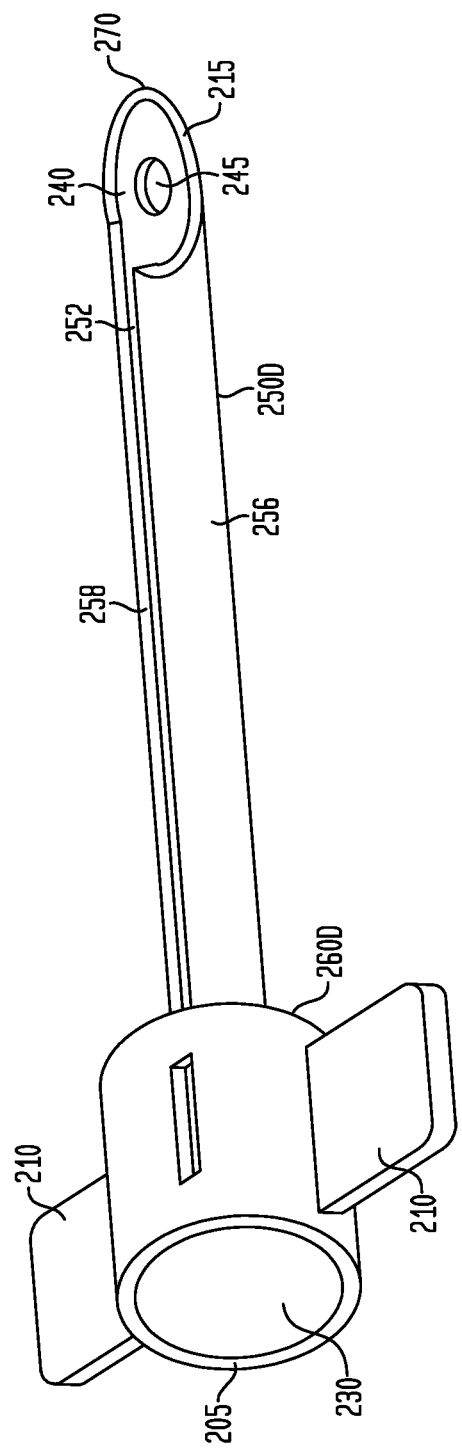
FIG. 29 is an isometric view illustrating the representative fourth embodiment of the outer needle assembly.
Figure 30:
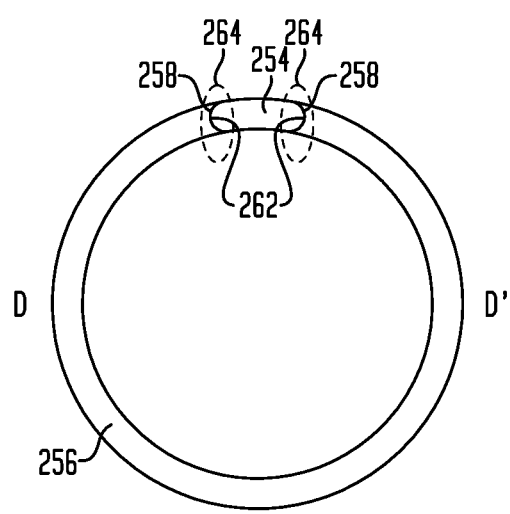
FIG. 30 is a cross-sectional view (through the D-D' plane) illustrating the representative third embodiment of the hemodialysis needle assembly (of FIG. 26) having the representative fourth embodiment of the outer needle assembly and the representative fifth embodiment of the integral needle tip protector in the second, extended arrangement, position or configuration.

FIG. 24 is an isometric view illustrating a representative third embodiment of a hemodialysis needle assembly 200D having a representative fourth embodiment of an outer needle assembly 260D and a representative fifth embodiment of an integral needle tip protector 100D in a first, retracted arrangement, position or configuration 50D. FIG. 25 is an elevational (side), cut-away view illustrating the representative third embodiment of the hemodialysis needle assembly 200D having the representative fourth embodiment of the outer needle assembly 260D and the representative fifth embodiment of the integral needle tip protector 100D of FIG. 24 in the first, retracted arrangement, position or configuration 50D. FIG. 26 is an isometric view illustrating the representative third embodiment of the hemodialysis needle assembly 200D having the representative fourth embodiment of the outer needle assembly 260D and the representative fifth embodiment of the integral needle tip protector 100D in the second, extended arrangement, position or configuration 55D. FIG. 27 is an isometric, cut-away view illustrating the representative third embodiment of the hemodialysis needle assembly 200D (of FIG. 26) having the representative fourth embodiment of the outer needle assembly 260D and the representative fifth embodiment of the integral needle tip protector 100D in the second, extended arrangement, position or configuration 55D. FIG. 28 is a cross-sectional view (through the C-C' plane) illustrating the representative third embodiment of the hemodialysis needle assembly 200D (of FIG. 26) having the representative fourth embodiment of the outer needle assembly 260D and the representative fifth embodiment of the integral needle tip protector 100D in the second, extended arrangement, position or configuration 55D, with the dashed lines indicating the portions of the needle tip cover 150D which are removed to show the cross section. FIG. 29 is an isometric view illustrating the representative fourth embodiment of the outer needle assembly 260D. FIG. 30 is a cross-sectional view (through the D-D' plane) illustrating the representative third embodiment of the hemodialysis needle assembly (of FIG. 26) having the representative fourth embodiment of the outer needle assembly and the representative fifth embodiment of the integral needle tip protector in the second, extended arrangement, position or configuration.

Referring to FIGS. 24-30, the third embodiment of a hemodialysis needle assembly 200D comprises an outer needle assembly 260D and an integral needle tip protector 100D, and except as described in greater detail below, generally functions and/or operates similarly to the hemodialysis needle assemblies 200 previously discussed, and common components are not separately discussed. The main differences in this embodiment of a hemodialysis needle assembly 200D is that the outer needle 250D includes a longitudinal slot (or longitudinal channel) 252 in the partially tubular wall 256 forming the outer needle 250D, and instead of a connecting rod 125, the integral needle tip protector 100D also comprises a sliding connector 254, which is insertable into and fills the longitudinal slot 252, with the sliding connector 254 slideable (using actuator 130D) in the longitudinal slot 252 between the first, retracted arrangement, position or configuration 50D and the second, extended arrangement, position or configuration 55D. Stated another way, the sliding connector 254 fills in (or seals) the otherwise open longitudinal slot 252 and thereby also forms part of the outer needle 250D; the sliding connector 254 is insertable into the slot 252, abutting the slot edges 258 of the wall 256 outer needle 250D, to create a complete tube or hollow cylinder for the outer needle 250D having a first lumen 230. As illustrated in FIG. 30, the edges 262 of the sliding connector 254 are configured to provide mating surfaces 264 with (and thereby seal against) the edges 258 of the longitudinal slot 252 of the wall 256 of the outer needle 250D. While the edges 262, 258 are illustrated as curved, those having skill in the art will recognize that many different surface shapes may be utilized equivalently, in addition to those illustrated, provided that the edges 262 of the sliding connector 254 are not sufficiently sharp to puncture or otherwise injure a vein, graft or fistula, for example.

As illustrated, the representative fifth embodiment of the integral needle tip protector 100D also has an actuator 130D, a sliding connector 254 (instead of a connecting rod 125) coupled to or integrally formed with the actuator 130D, and a needle tip cover 150D coupled to or integrally formed with the sliding connector 254. For this embodiment, the needle tip cover 150D is illustrated as also having a ring configuration or ring shape, including a ring-shaped, smooth, curved or beveled surface 105, but any of the various other integral needle tip protectors 100 may be utilized equivalently. In addition, for this embodiment, depending upon the size (longitudinal dimension) of the needle tip cover 150D, there may be lateral space between the needle tip cover 150D and the sharp first aperture (opening, inlet or outlet) 240, also allowing for additional blood or other fluid flow through the first lumen 230 when the integral needle tip protector 100D is in the second, locked and extended arrangement, position or configuration.

In use, the hemodialysis needle assembly 200D in the first, retracted arrangement, position or configuration 50D is also inserted into a vein, fistula or graft of a patient. Using the actuator 130D, sliding in the channel 220D, the integral needle tip protector 100D is advanced (forward) into the second, extended arrangement, position or configuration 55D, and remains in this second, extended arrangement, position or configuration 55D for the duration of the dialysis session. In doing so, the sliding connector 254 also advances, sliding forward in the longitudinal slot 252, and moving or projecting the needle tip cover 150D forward to cover the sharp needle tip (or point) 215 of the outer needle 250D, as illustrated in FIGS. 26-28.

As mentioned above, the integral needle tip protector 100, 100A, 100B, 100C, 100D, is comprised of any suitable material, such as a biocompatible or inert polymer or plastic, such as polystyrene or polytetrafluoroethylene (PTFE or Teflon), carbon fiber, or any type of biocompatible or inert metal or alloy, such as steel, titanium, aluminum, etc., for example and without limitation. Other representative examples of biocompatible or inert polymers include, but are not limited to, fluorinated polymers or copolymers such as poly(vinylidene fluoride), poly(vinylidene fluoride-co-hexafluoropropene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly (caprolactones); poly(lactide-co-glycolide); poly (hydroxybutyrates); poly(hydroxybutyrate-co-valerate); poly(dioxanones); poly(orthoesters); poly(anhydrides); poly (glycolic acid); poly(glycolide); poly(D,L-lactic acid); poly (D,L-lactide); poly(glycolic acid-cotrimethylene carbonate); poly(phosphoesters); poly(phosphoester urethane); poly(trimethylene carbonate); poly(iminocarbonate); poly(ethylene); and any derivatives, analogs, homologues, congeners, salts, copolymers and combinations thereof.

The biocompatible or inert polymers may also include, but are not limited to, poly(propylene) copoly(ether-esters) such as, for example, poly(dioxanone) and poly(ethylene oxide)/poly(lactic acid); poly(anhydrides), poly(alkylene oxalates); poly(phosphazenes); poly(urethanes); silicones; silicone rubber; poly(esters); poly(olefins); copolymers of poly(isobutylene); copolymers of ethylene-alphaolefin; vinyl halide polymers and copolymers such as poly(vinyl chloride); poly(vinyl ethers) such as, for example, poly (vinyl methyl ether); poly(vinylidene halides) such as, for example, poly(vinylidene chloride); poly(acrylonitrile); poly(vinyl ketones); poly(vinyl aromatics) such as poly (styrene); poly(vinyl esters) such as poly(vinyl acetate); copolymers of vinyl monomers and olefins such as poly (ethylene-co-vinyl alcohol) (EVAL), copolymers of acrylonitrile-styrene, ABS resins, and copolymers of ethylene-vinyl acetate; and any derivatives, analogs, homologues, congeners, salts, copolymers and combinations thereof.

The biocompatible or inert polymers may further include, but are not limited to, poly(amides) such as Nylon 66 and poly(caprolactam); alkyd resins; poly(carbonates); poly (oxymethylenes); poly(imides); poly(ester amides); poly (ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof. At least one of polymers can be a poly(ester amide), a poly(lactide) or a poly(lactide-co-glycolide) copolymer; and any derivatives, analogs, homologues, congeners, salts, copolymers and combinations thereof.

Numerous advantages of the representative embodiments are readily apparent. The various representative embodiments provide a hemodialysis needle assembly 200 which reduces the likelihood of puncturing the fistula or graft and causing a hemorrhage and possibly also a fistula thrombosis. Such representative embodiments of a hemodialysis needle assembly 200-200D are comparatively easy for medical personnel to insert into the lumen of the fistula or graft, and extend the integral needle tip protector 100-100D into the second, locked and extended arrangement or configuration. The representative embodiments of a hemodialysis needle assembly 200-200D further provide protection to the medical personnel from exposure to the sharp needle tip 215 when the hemodialysis needle assembly is removed from the patient, as the integral needle tip protector 100-100D remains locked in the second, locked and extended arrangement or configuration.

It should also be noted that, unless the context otherwise indicates, reference to any one of the hemodialysis needle assemblies 200-200D and their components shall be understood to mean and include any other hemodialysis needle assembly 200-200D and its components, reference to any one of the integral needle tip protectors 100-100D and their components shall be understood to mean and include any other integral needle tip protector 100-100D and its components, and reference to any one of the outer needle assemblies 260-260D and their components shall be understood to mean and include any other outer needle assembly 260-260D and its components, without limitation.

The present disclosure is to be considered as an exemplification of the principles of the invention and is not intended to limit the invention to the specific embodiments illustrated. In this respect, it is to be understood that the invention is not limited in its application to the details of construction and to the arrangements of components set forth above and below, illustrated in the drawings, or as described in the examples. Systems, methods and apparatuses consistent with the present invention are capable of other embodiments and of being practiced and carried out in various ways.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. In addition, the various Figures are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment of the present invention and not necessarily in all embodiments, and further, are not necessarily referring to the same embodiment. Furthermore, the particular features, structures, or characteristics of any specific embodiment of the present invention may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

It will also be appreciated that one or more of the elements depicted in the Figures can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "couplable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. In addition, every intervening sub-range within range is contemplated, in any combination, and is within the scope of the disclosure. For example, for the range of 5-10, the sub-ranges 5-6, 5-7, 5-8, 5-9, 6-7, 6-8, 6-9, 6-10, 7-8, 7-9, 7-10, 8-9, 8-10, and 9-10 are contemplated and within the scope of the disclosed range.

Furthermore, any signal arrows in the drawings/Figures should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

It is claimed:

1. A needle assembly for medical or surgical use, the needle assembly comprising:
   an outer needle assembly comprising:
      an outer needle comprising:
      a first lumen;
      a first aperture with a sharp needle tip at a first distal end of the outer needle; and
      a second aperture arranged opposite the first aperture; and
   an integral needle tip protector arranged within the first lumen and moveable within the first lumen between a retracted configuration and an extended configuration, the integral needle tip protector comprising:
   a needle tip cover having a first end and a second end, the needle tip cover comprising a ring configuration having a first opening and a second opening, the first opening configured to align with the first aperture in the extended configuration and the second opening configured to align with the second aperture in the extended configuration.

2. The needle assembly of claim 1, wherein the needle tip cover further comprises a smooth or beveled surface at the first end of the needle tip cover.

3. The needle assembly of claim 1, wherein the outer needle assembly further comprises:
   one or more third apertures arranged on one or more lateral sides of the outer needle assembly spaced apart from the first and second apertures.

4. The needle assembly of claim 1, wherein the integral needle tip protector further comprises:
   an actuator arranged or coupled at the second end of the integral needle tip protector; and
   a sliding connector or a connecting rod coupling the actuator to the needle tip cover.

5. The needle assembly of claim 4, wherein:
   the actuator further comprises a recess or a detent; and
   wherein the outer needle assembly further comprises a mating detent or recess coupleable to the recess or detent of the actuator.

6. The needle assembly of claim 4, wherein the outer needle assembly further comprises:
   a connector coupled to a second end of the outer needle to couple the outer needle to a syringe or tubing; and
   one or more handles coupled to the connector.

7. The needle assembly of claim 6, wherein the connector further comprises:
   a first longitudinal channel; and
   a second transverse channel;
   wherein the actuator is moveable within the first longitudinal channel to move the integral needle tip protector from the retracted configuration to the extended configuration.

8. The needle assembly of claim 7, wherein the actuator is moveable within the second transverse channel to lock the integral needle tip protector in the extended configuration.

9. The needle assembly of claim 1, wherein the ring configuration further comprises a beveled ring having a second lumen, and wherein the beveled ring at least partially abuts the first lumen.

10. The needle assembly of claim 1, wherein in the extended configuration, the needle tip cover extends longitudinally over the sharp needle tip at the first end of the outer needle.

11. The needle assembly of claim 1, wherein the needle tip cover further comprises:
    one or more detents arranged on one or more sides of the needle tip cover, each of the one or more detents having a smooth surface; and
    wherein the outer needle further comprises:
    one or more mating recesses arranged on one or more sides of the outer needle to couple to the one or more detents in the extended configuration.

12. The needle assembly of claim 1, wherein the outer needle further comprises:
    one or more detents arranged on one or more sides of the outer needle and extending within the first lumen; and
    wherein the needle tip cover further comprises:
    one or more mating recesses arranged on one or more sides of the needle tip cover to couple to the one or more detents in the extended configuration.

13. The needle assembly of claim 1, wherein the second opening is at least partially congruent with the second aperture, and the first opening is at least partially congruent with the first aperture.

14. The needle assembly of claim 1, wherein the outer needle assembly further comprises:
    a spring coupled to the integral needle tip protector; and
    an actuator to release the spring to move the integral needle tip protector from the retracted configuration to the extended configuration.

15. The needle assembly of claim 1, wherein the outer needle further comprises a longitudinal slot, and the integral needle tip protector further comprises a sliding connector coupled to the needle tip cover, the sliding connector slideable within the longitudinal slot.

16. A needle assembly for medical or surgical use, the needle assembly comprising:
    an outer needle assembly comprising:
       an outer needle comprising:
       a first lumen;
       a first aperture with a sharp needle tip at a first end of the outer needle;
       a second aperture arranged opposite the first aperture;
       a longitudinal slot; and
       a connector coupled to a second end of the outer needle; and
    an integral needle tip protector arranged within the first lumen and moveable within the first lumen between a retracted configuration and an extended configuration, the integral needle tip protector comprising:
    a needle tip cover arranged at a first end of the integral needle tip protector, the needle tip cover having a ring configuration with a first opening and a second opening and with a smooth or beveled distal surface; and
    a sliding connector, the sliding connector slidable in the longitudinal slot.

17. The needle assembly of claim 16, wherein the integral needle tip protector further comprises:
    an actuator at a second end of the integral needle tip protector, the actuator is moveable within the first longitudinal channel to slide the sliding connector in the longitudinal slot and move the integral needle tip protector from the retracted configuration to the extended configuration.

18. The needle assembly of claim 16, wherein in the extended configuration, the needle tip cover extends longitudinally over the sharp needle tip at the first distal end of the outer needle.

19. The needle assembly of claim 16, wherein the longitudinal slot further comprises a first plurality of edges, and wherein the sliding connector has a second plurality of edges having mating surfaces to the first plurality of edges.

20. A needle assembly for medical or surgical use, the needle assembly comprising:
   an outer needle assembly comprising:
      an outer needle comprising:
         a first lumen;
         a first aperture with a sharp needle tip at a first distal end of the outer needle;
         a second aperture arranged opposite the first aperture;
         a longitudinal slot; and
      a connector coupled to a proximal end of the outer needle;
   and
   an integral needle tip protector arranged within the first lumen and moveable within the first lumen between a retracted configuration and an extended configuration, the integral needle tip protector comprising:
      a needle tip cover having a ring configuration with a second lumen and configured to shield the sharp needle tip in the extended configuration, the needle tip cover comprising:
         a smooth or beveled distal surface;
         a first opening configured to align with the first aperture in the extended configuration; and
         a second opening configured to align with the second aperture in the extended configuration;
      an actuator arranged or coupled at a proximal end of the integral needle tip protector; and
      a sliding connector coupling the actuator to the needle tip cover, the sliding connector slidable in the longitudinal slot.

* * * * *